United States Patent
Christensen et al.

(10) Patent No.: US 6,632,669 B2
(45) Date of Patent: Oct. 14, 2003

(54) PLANT KINASES AND METHODS OF MODULATION OF THEIR ACTIVITY IN PLANTS

(75) Inventors: Susan K. Christensen, Los Angeles, CA (US); Joanne Chory, Del Mar, CA (US); Detlef Weigel, Solana Beach, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/727,405

(22) Filed: Nov. 29, 2000

(65) Prior Publication Data

US 2002/0104118 A1 Aug. 1, 2002

Related U.S. Application Data

(60) Provisional application No. 60/167,926, filed on Nov. 29, 1999.

(51) Int. Cl.⁷ .......................... C12N 5/04; C12N 15/00; C07H 21/02; C07H 21/04; A01H 11/00
(52) U.S. Cl. ...................... 435/419; 800/295; 536/23.1; 536/23.6; 536/23.2; 435/320.1
(58) Field of Search .................. 800/298, 295, 800/290; 536/23.1, 23.6; 435/419, 468, 69.1, 469, 23.2

(56) References Cited

PUBLICATIONS

Christensen et al (2000, Cell 100:469–478).*
Bowie et al (1990, Science 247:1306–10).*
McConnell et al (2001, Nature 411 (6838):709–713).*
Fourgoux–Nicol et al (1999, Plant Molecular Biology 40: 857–872).*
Huala et al (1997, Science 278:2120–2123; NCBI Database, Accession No. AF030864).*
Bennett, et al. *Morphogenesis in pinoid mutants of Arabidopsis thaliana*, The Plant Journal, (1995) 8(4), 505–520.
Chen, et al., *The Arabidopsis thaliana AGRAVITROPIC 1 gene encodes a component of the polar–auxin–transport efflux carrier*, Proc. Natl. Acad. Sci. USA, Vo. 95, pp 15112–15117, Dec. 1998.
Christie et al., *Arabidopsis NPH1: A Flavoprotein with the Properties of a Photoreceptor for Phototropism*, Science, vol. 282, Nov. 27, 1998, pp 1698–1701.
Gälweiler, et al. *Regulation of Polar Auxin Transport by AtPIN1 in Arabidopsis Vascular Tissue*, Science, vol. 282, Dec. 18, 1998, pp. 2226–2230.

Hanks, et al., *The Protein Kinase Family: Conserved Features and Deduced Phylogeny of the Catalytic Domains*, Science, vol. 241, Jul. 1, 1988, pp. 42–52.
Luschnig, et al., *EIR1, a root–specific protein involved in auxin transport, is required for gravitropism in Arabidopsis thaliana*, Genes & Development, Mar. 30, 1998, pp. 2175–2187.
Müller, et al., *AtPIN2 defines a locus of Arabidopsis for root gravitropism control*, The EMBO Journal, vol. 17, No. 23, pp. 6903–6911, 1998.
Okada, et al., *Requirement of the Auxin Polar Transport System in Early Stages of Arabidopsis Floral Bud Formation*, The Plant Cell, vol. 3, Jul. 1991, pp 677–684.
Przemeck, et al., *Studies on the role of the Arabidopsis gene MONOPTEROS in vascular development and plant cell axialization*, Planta (1996) 200:229–237.
Bennett, et al., *Morphogenesis in pinoid mutants of Arabidopsis thailana*; The Plant Journal. 8(4):505–20 (1995).
Chen, et al., *The Arabidopsis thaliana AGRAVITROPIC 1 gene encodes a component of the polar–auxin–transport efflux carrier*; Proc. Natl. Acad. Sci. USA, vol. 95:15112–117 (1998).
Galweiler, et al., *Regulation of Polar Auxin Transport by AtPIN1 in Arabidopsis Vascular Tissue*; SCIENCE. vol. 282 (1998).
Luschnig, et al., *EIR1, a root–specific protein involved in auxin transport, is required for gravitropism in Arabidopsis thailana*: Genes & Development. 12:2175–87 (1998).
Hanks, et al., *The Protein Kinase Family: Conserved Features and Deduced Phylogeny of the Catalytic Domains*; Science. vol. 241:42–52.
Müller, et al., *AtPIN2 defines a locus of Arabidopsis for root gravitropism control*: EMBO Journal. vol. 17–23:6903–6911 (1998).
Okada, et al., *Requirement of the Auxin Polar Transport System in Early Stages of Arabidopsis Floral Bud Formation*; The Plant Cell. vol. 3:677–684.
Przemeck, et al., *Studies on the role of the Arabidopsis gene MOMOPTEROS in vascular development and plant cell axialization*; Planta. 200:229–237 (1996).

* cited by examiner

*Primary Examiner*—Phuong T. Bui
*Assistant Examiner*—Stuart F. Baum
(74) *Attorney, Agent, or Firm*—Knobbe, Martens, Olson & Bear, LLP

(57) ABSTRACT

The invention disclosed herein provides a purified polynucleotide, wherein the polynucleotide comprises a nucleic acid encoding a plant DFD kinase polypeptide, methods for using same, and transgenic plants containing the polynucleotide.

13 Claims, 6 Drawing Sheets

FIG. 1

| Allele | Nucleotide change; Predicted protein change |
|---|---|
| *pid1-1* | CGA→TGA;R53stop |
| *pid1-2* | GGG→AGG;G380R |
| *pid1-3* | CTC→TTC;L226F |
| *pid1-4* | AGA→AAA;R378K |
| *pid1-5* | GAG→AAG;E128K |
| *pid1-6* | GGA→TAG;R63stop |
| *pid1-7* | TACGAGATGATATATGGCAAGAC TCCGTTCGTTGCGCC deletion; frameshift |
| *pid1-8* | CCA→CAA;P300Q |
| *pid1-9* | CGATTCTCCCTCTCTTCCGCCAG deletion,T-DNA insertion at exon-intron boundary; frameshift |
| *pid1-10* | GGC→AGC;G84S |

FIG. 5

| FIG. 5A |
|---------|
| FIG. 5B |

```
cctcttccatctctcaaacttctgaaaatctttctttctcaatcataaacctaaatcttcatctcttcagatcagaactaatgtccattc     99
aaagacaccctgtcctgtcttcatctctgtcattagtctctctgttttcagattccaatttttttcttgaattatctcttagccattt ctt gatttaact  198
tcgatttcccggcgatgttacgagaatcagacggtgagatgagtttaggaacaacaaactcaccgataagcagcggaacagagagttgcagcagttc     297
              M  L  R  E  S  D  G  E  M  S  L  G  T  T  N  S  P  I  S  S  G  T  E  S  C  S  S  F      28
agccggttatcattcgacgcgccgccgcctcaactatcccgaagaagaaagcttcctttctctcaacctcaccgatcctcagatttgcttacgcagag     396
 S  R  L  S  F  D  A  P  P  S  T  I  P  E  E  E  S  F  L  S  L  K  P  H  R  S  S  D  F  A  Y  A  E      61
     stop
atccgaagacgaaaaacaaggctaacttgcgcctcatgcgctgtatcgcggccgggacatcggtgcgacagttactatgccgtcta     495
 I  R  R  K  K  Q  G  L  T  F  R  D  F  R  L  M  R  R  I  G  A  G  D  I  G  T  V  Y  L  C  R  L      94
gccggagcgaagaagagcgagctcgtgagctcgtatttgcgatgaaagttgtggataaagaagctcttgcgttgaagaagaagcatagagcagaatg     594
 A  G  D  E  E  E  S  R  S  S  Y  F  A  M  K  V  V  D  K  E  A  L  A  L  K  K  K  M  H  R  A  E  M    127
 K
gagaaacgatttgaaatgcttgaccatcatttgccactctttacgctgagttgaagcctgagttgaagcctcacattctcttgatcgttatgaatattgc     693
 E  K  T  I  L  K  M  L  D  H  P  R  L  P  T  L  Y  A  E  F  E  A  S  H  F  S  C  I  V  M  E  Y  C    160
tccggtgtgatttacactctccgtcatagacaacctcacggcattcctccctcttccgccagatttatgccgaagttctagtggcgtta     792
 S  G  G  D  L  H  S  L  R  H  R  Q  P  H  R  R  F  S  L  S  S  A  R  F  Y  A  A  E  V  L  V  A  L    193
                                                                                                    *
gaatatctacacatgttggtatcatctcagatctgaagctgaaaatatcttagttagatccgacggtcacattatgctctctgacttgacctc     891
 E  Y  L  H  M  L  G  I  I  Y  R  D  L  K  P  E  N  I  L  V  R  S  D  G  H  I  M  L  S  D  F  D  L    236
tctctatgctccgactcaatcgcagccgttaatcttcctcgtcttcgccggagaatcaacaactccgttcaccgcgacgattcactcgtctcgctaga     990
 S  L  C  S  D  S  I  A  A  V  E  S  S  S  S  P  E  N  Q  Q  L  R  S  P  R  R  F  T  R  L  A  R      269
```

FIG. 5A

```
cttttccacgagtcttgcgggtctaaaaggttcagacttttagaacttgttgctgaaccggttactgcccggtccggttcgtt    1089
 L  F  Q  R  V  L  R  S  K  K  V  Q  T  L  E  P  T  R  L  F  V  A  E  P  V  T  A  R  S  G  S  F  V    302
                       *                                               *                *    *
ggtacgcatgaatacgtggcaccagaagttgcttcaggtggatcacatggtaatgccgtttgactggttctctacgagatgata    1188
 G  T  H  E  Y  V  A  P  E  V  A  S  G  G  S  H  G  N  A  V  D  W  A  F  G  V  F  L  Y  E  M  I    335
                   Q
tatgcaagactccgttgctgccgactaatgacgtcattctccgtaacattgtgaaaagacagttgagtttcccgactgattcgccggcgactatg    1287
 Y  G  K  T  P  F  F  V  A  P  T  N  D  V  I  L  R  N  I  V  K  R  E  L  S  F  P  T  D  S  P  A  T  M    368
                                                 K           R
tttgagcttcatgcgcggaatttgatttccgggttgcttaacaaagatccgactaaaagacttggtcacgcgaggtgcggaggttaaagtgcat    1386
 F  E  L  H  A  R  N  L  I  S  G  L  L  N  K  D  P  T  K  R  L  G  S  R  R  G  A  A  E  V  K  V  H    401
                                                       R
cctttttcaaggtctaaactttgctcattcgtacgcttactcctccgtcttcctgtcttcaagaagccgatgaatcggcgacgttt    1485
 P  F  F  K  G  L  N  F  A  L  F  R  T  L  T  P  P  E  I  P  S  S  V  V  K  K  P  M  K  S  A  T  F    434
agtggtagaagtagtaacaaccagccgttcgattactttgaacgttttctacgtgttagtctgttttagctgtacat    1584
 S  G  R  S  S  N  K  P  A  A  F  D  Y  F                                                              448
attccctcgaagctgtcctttttcgtcttaattttaaaatttcgttaatctgac    1643
```

FIG. 5B

PLANT KINASES AND METHODS OF MODULATION OF THEIR ACTIVITY IN PLANTS

RELATED APPLICATIONS

This invention claims priority under 35 U.S.C. §119(e) to provisional patent application No. 60/167,926, filed Nov. 29, 1999, and which is hereby incorporated by reference in its entirety.

GOVERNMENT RIGHTS

This invention was made with government support under National Science Foundation (NSF) grant #IBN-9723818, NSF grant #BIR-9627087, and NSF grant #MCB-9631390. The government may have certain rights in the invention.

BACKGROUND OF THE INVENTION

1. Field of the Invention

The present invention relates generally to plant growth and development and more specifically to identification of novel plant kinases and methods of identifying compounds that modulate the activity of such kinases in plants.

2. Description of the Related Art

Phosphorylation by protein kinases is one of the most common and important regulatory mechanisms in signal transmission. Plant genomes encode many protein kinases. Some of the plant kinases are homologues of kinases found in animals and fungi, while others have novel structures. Kinases comprise the largest known protein group, a super family of enzymes with widely varied functions and specificities. Kinases covalently modify proteins and peptides by the attachment of a phosphate group to one or more sites on the substrate protein.

Many of the known protein kinases use adenosine triphosphate (ATP) as the phosphate donor and place the gamma phosphate from the ATP onto an acceptor amino acid. The amino acids that can act as acceptors of the gamma phosphate group are Serine (Ser), Theronine (Thr), Tyrosine (Tyr), or Histidine (His). The majority of protein kinases known can be categorized as either Ser/Thr kinases or Tyr kinases. The Histidine kinases, originally identified in bacterial two-component systems, have recently been found as part of signaling pathways in plants and fungi.

Protein kinases can be further subdivided into families based on the amino acid sequences surrounding or inserted into the kinase catalytic domain. The function of these sequences surrounding the catalytic domain have been shown to allow regulation of the kinase as it recognizes its target substrate protein (Hardie, G and Hanks, S. (1995) The Protein Kinase Facts Books, Vol I:7–20 Academic Press, San Diego, Calif.).

The primary structure of the kinase catalytic domain is conserved and can be further subdivided into 11 subdomains. Each of these 11 subdomains contains sequence motifs that are highly conserved or invariant (Hardie, G and Hanks, S. (1995) The Protein Kinase Facts Books, Vol I:7–20 Academic Press, San Diego, Calif.). One such motif found in kinases identified to date is an invariable domain comprising asparagine, phenylalanine and glycine residues (DFG domain) surrounded by several conserved residues (Hunter T., (1997) Philos Trans R Soc Lond B Biol Sci. 353(1368):583–605, Hunter T. (1995) Cell. 80(2):225–36; van der Geer P, et al. (1994) Annu Rev Cell Biol. 10:251–337).

Studies have shown that kinases are key regulators of many cellular functions, such as: cell proliferation, cell differentiation, signal transduction, transcriptional regulation, cell motility, and cell division. Few, if any physiological processes exist in eukaryotes that are not dependent on phosphorylation.

Of particular importance in intracellular signaling are the mitogen-activated protein kinases (MAPKs). MAPKs are also members of the Ser/Thr family of protein kinases. MAPKs play a central role in the transduction of diverse extracellular stimuli, including signals that regulate development and differentiation, into intracellular responses in yeast and animals cells via phosphorylation cascades. Homologues of the MAPKs found in animals and yeast have been found in plants. Previous studies have suggested the involvement of MAP kinase cascades in the regulation of auxin signaling. In vitro phosphorylation of a bacterially produced Arabidopsis MAP kinase by a tobacco cell extract is three to four-fold more effective after treatment of protoplasts with the synthetic auxin 2,4-D, as compared to extracts from auxin-starved cultures (Mizoguchi et al. (1994) Plant J. 5:111–122). The importance of MAP kinase phosphorylation has also been demonstrated by over-expression in maize protoplasts of the catalytic domain of the tobacco MAPKK kinase NPK1, which blocks transcription from the auxin-responsive GH3 promoter (Kovtun et al. (1998) Nature 395:716–720). A role for protein phosphorylation in auxin transport has also been inferred from the discovery that the Arabidopsis gene ROOTS CURL IN NPA 1 (RCN1) encodes a regulatory subunit of protein phosphatase 2A (Garbers et al. (1996) EMBO J. 15:2115–2124).

Plant growth and development are governed by complex interactions between environmental signals and internal factors. Light regulates many developmental processes throughout the plant life cycle, from seed germination to floral induction (Chory, J. Trends Genet., 9:167, 1993; McNellis and Deng, Plant Cell, 7:1749, 1995), and causes profound morphological changes in young seedlings. In the presence of light, hypocotyl growth is inhibited, cotyledons expand, leaves develop, chloroplasts differentiate, chlorophylls are produced, and many light-inducible genes are coordinately expressed. It has been suggested that plant hormones, which are known to affect the division, elongation, and differentiation of cells, are directly involved in the response of plants to light signals (P. J. Davies, Plant Hormones: Physiology, Biochemistry and Molecular Biology, pp 1–836, 1995; Greef and Freddericq, Photomorphogenesis, pp 401–427, 1983). The interactions between phototransduction pathways and plant hormones however are not well understood.

Auxin is one of the classical plant hormones and regulates many aspects of plant development, including cell division, cell elongation and cell differentiation in both the root and the shoot of plants (M. Estelle, Bioessays 14:439–44, 1992 and L. Hobbie et al., Plant Mol. Biol. 26:1499–519, 1994). For example, apical dominance as well as lateral root growth are under auxin control, and manipulation of auxin signaling can be used to affect growth of both the shoot and the root system.

From its point of synthesis at the plant apex (Davies, P. J. (1995) The plant hormones: Their nature, occurrence, and functions. In Plant Hormones: Physiology, Biochemistry and Molecular Biology, P. J. Davies, ed. (Netherlands: Kluwer Academic Publishers), pp. 1–12), the phytohormone auxin is directionally transported through the plant body to effect an astonishing variety of morphological processes. Auxin is required early in development to establish the bilateral axis of the developing embryo Hadfi et al. (1998) Development 125:879–887). Later, auxin participates in vascular element patterning and differentiation (Aloni, R. (1995). Biochemistry and Molecular Biology, P. J. Davies, ed. (Netherlands: Kluwer Academic Publishers), pp. 531–545), lateral organ outgrowth in the root and shoot (Okada et al. (1 991) Plant Cell 3:677–684; Celenza et al. (1995) Genes Dev. 9:2131–2142), and local growth responses to external stimuli such as light and gravity (Kaufman et al. (1995). Hormones and the orientation of growth. In Plant Hormones: Physiology, Biochemistry and Molecular Biology, P. J. Davies, ed. (Netherlands: Kluwer Academic), pp. 547–570).

While an understanding of the mechanisms of auxin action at the molecular level is preliminary, genetic and biochemical approaches have begun to reveal discrete aspects of auxin transport, signaling and response. Two related Arabidopsis proteins, PINFORMED (PIN) and ETHYLENE INSENSITIVE ROOT 1 (EIR1)/AGRAVITROPIC1 (AGR1)/PIN2, which share homology with bacterial membrane transporters, function as auxin efflux carriers in the shoot and root, respectively (Chen et al. (1998) Proc. Natl. Acad. Sci. USA 95:15112–15117; G älweiler et al. (1998) Science 282:2226–2230; Luschnig et al. (1998) Genes Dev. 12:2175–2187; Müller et al. (1998) EMBO J. 17:6903–6911). The auxin influx carrier AUXIN INSENSITIVE 1 (AUX1), which shares homology with plant and fungal amino acid permeases, functions in root gravitropism (Bennett et al. (1996) Science 273:948–950; Marchant et al. (1999) EMBO J. 18:2066–2073). TRANSPORT INHIBITOR RESPONSE 3 (TIR3) has been implicated in auxin transport in both the root and the shoot. tir3 mutants have fewer binding sites than wild type for the auxin transport inhibitor NPA (naphthylphthalamic acid), suggesting that the TIR3 gene product either encodes or regulates an NPA binding protein (Ruegger et al. (1997) Plant Cell 9:745–757). An auxin receptor has not been unambiguously identified, but overexpression of the auxin-binding protein ABP1 affects cell expansion, a transcription-independent auxin-regulated process (Jones et al. (1998) Science 282:1114–1117).

Apart from proteins involved in auxin transport and binding, several classes of auxin-signaling molecules have been identified. One class includes regulators of protein stability such as AUXIN RESISTANT 1 (AXR1) and TIR1. These two proteins are components of the RUB conjugation pathway, which is analogous to and converges with the ubiquitin pathway (Lammer et al. (1998) Genes Dev. 12:914–926; Liakopoulos et al. (1998) EMBO J. 17:2208–2214). TIR1 is an F-box protein that together with SKP1 and Cdc53 constitutes an E3 ubiquitin ligase complex (Patton et al. (1998) Genes Dev. 12:692–705; Gray et al. (1999) Genes Dev. 13:1678–1691). The only identified target for RUB modification is the Cdc53 subunit of the E3 complex itself, the functional significance of which is unknown (Lammer et al., 1998; Liakopoulos et al., 1998).

Another class of auxin signaling molecules comprises the ARF (Auxin Response Factor) and Aux/IAA families of transcription factors (Guilfoyle et al. (1998) Plant Physiol. 118:341–347). ARFs bind to auxin response elements through an N-terminal DNA binding domain, while the carboxy-terminus contains two protein-protein interaction domains that are also found in the Aux/IAA family of early auxin-response genes. In vitro homodimerization and heterodimerization within each family, as well as interactions between the families, suggest that combinatorial action of these proteins confers cell or tissue specificity in auxin response (Kim et al. (1997) Proc. Natl. Acad. Sci. USA 94:11786–11791; Ulmasov et al. (1997a) Science 276:1865–1868; Ulmasov et al. (1997b) Plant Cell 9:1963–1971; Ulmasov et al. (1999) Plant J. 19:309–319). Although ARFs and Aux/IAAs were initially identified by biochemical methods, several Arabidopsis mutants with defects in auxin signaling have subsequently been shown to carry lesions in ARF or Aux/IAA genes (Hardtke and Berleth (1998) EMBO J. 17:1405–1411; Rouse et al. (1998) Science 279:1371–1373; Tian and Reed (1999) Development 126:711–721). One example is the MONOPTEROS (MP) gene, which encodes ARF5 and whose loss of function in the shoot results in a pin-like inflorescence similar to that seen in pin mutants, or in plants treated with polar auxin transport inhibitors (Okada et al., 1991; Berleth and Jurgens (1993) Development 118:575–587).

SUMMARY OF THE INVENTION

The invention disclosed herein is based on the discovery that an otherwise conserved motif in protein kinases is modified in various plant kinases. This conserved motif, the "DFD" domain, has been found in several plant kinases and is termed the "DFG" domain. One such exemplary plant kinase is identified in the present invention the PINOID (PID) gene, which encodes an auxin signaling and/or response protein.

PID gene encodes a member of a newly identified plant-specific serine-threonine protein kinase family. PID encodes a protein kinase, but belongs to a different class of serine-threonine kinases than the MAP, MAPK, or MAPKK kinases. PID contains 13 of the 14 invariant residues found in fungal and metazoan protein kinases (Hanks et al., 1988). The single exception is the replacement by aspartate of the invariant glycine of the DFG motif found in the consensus sequence of catalytic subdomain VII. The DFD motif of PID is identified in the present application as being present in several other putative plant kinases. At least one of these kinases, NPH1, functions in blue-light mediated phototropism and encodes a functional kinase (Christie et al. (1998) Science 282:1698–1701).

In contrast to PIN and MP, which are expressed in the vasculature of the inflorescence stem as well as in developing primordia. This expression pattern is PID is predominantly expressed in anlagen of lateral primordia, consistent with PID affecting downstream events in auxin signaling. In contrast to pin and mp mutants, which have substantially decreased auxin flow in the inflorescence, pid mutants show only a modest reduction in polar auxin transport (Okada et al., (1991); Bennett et al. (1995) Plant J. 8:505–520; Przemeck et al. (1996) Planta 200:229–237). Moreover, PID overexpression results in shoot and root phenotypes similar to those of auxin-insensitive mutants, indicating that PID regulates auxin signaling.

One embodiment of the invention disclosed herein provides an assay for identifying plant kinases, specifically, DFD kinases. The plant kinase assay includes screening nucleic acid obtained from a plant in order to identify a nucleotide sequence that encodes a contiguous DFD amino acid sequence in a region of the nucleotide sequence ordinarily known to encode a "DFG" sequence. The presence of a DFD catalytic domain, in addition to the presence of other kinase structural markers, indicates that the nucleic acid encodes a plant kinase, or a fragment thereof.

In another embodiment, the invention provides methods for identifying compounds that modulate the activity of DFD plant kinases. The kinase assays of the invention include incubating at least one putative kinase-modulating compound and a DFD plant kinase polypeptide containing a DFD motif under conditions sufficient for the components to interact, and determining kinase activity in the presence and the absence of the compound, wherein a difference in activity is indicative of a compound that modulates kinase activity of a plant DFD kinase. An exemplary DFD kinase that can be utilized in the method of the invention is a PINOID polypeptide. Compounds or agents, including small molecules, peptides or nucleic acid sequences, that affect DFD kinase activity by binding to a DFD kinase can be identified by the method of the invention. A complex between a DFD kinase and a test compound or agent can be identified and the binding agent isolated therefrom. Such compounds or agents can be further evaluated to determine whether they bind and/or affect DFG kinase activity.

In another embodiment, there are provided methods for modulating the level or activity of DFD kinases, comprising exposing DFD kinases to DFD inhibitors. In a preferred embodiment of the present invention, there are provided methods for inhibiting the growth or exterminating plants expressing DFD kinases. Preferably, the inhibitor will bind DFD kinases, more preferably, the inhibitor will be specific for DFD kinases and will not bind or affect DFG kinases. Such inhibitors are especially useful in methods for selectively growing plants expressing kinases containing the DFD domain.

In another embodiment, the invention provides a method for producing a genetically modified plant characterized as having early or increased loss of apical dominance, such as increased branching and/or lateral root growth, as compared to a wild-type plant. The method includes transferring at least one copy of a DFD kinase-encoding polynucleotide operably associated with a promoter to a plant cell to obtain a transformed plant cell and producing a plant from the transformed plant cell. Such genetically modified plants may exhibit increased branching and/or lateral root growth. An exemplary DFD kinase includes members of the PINOID gene family.

In another embodiment, the invention provides a method for genetically modifying a plant cell such that the plant produced from the cell is characterized phenotypically by increased branching and/or lateral root growth as compared to a wild-type plant. The method comprises contacting a plant cell with at least one copy of a DFD kinase-encoding polynucleotide to obtain a transformed plant cell and growing the transformed plant cell under plant forming conditions to obtain a plant having increased shoot architecture or root growth.

In another embodiment, the invention provides a method for obtaining a genetically modified plant characterized as having increased apical dominance (e.g., decreased branching and/or lateral root growth) as compared to a wild-type plant. The method comprises transferring at least one loss-of-function dominant negative variant of a DFD kinase-encoding polynucleotide, operably associated with a promoter, to a plant cell to obtain a transformed plant cell and producing a plant from the transformed plant cell having increased apical dominance (i.e., due to overexpression of the loss-of-function variant in the plant).

In yet another embodiment, the invention provides a method for producing a plant characterized as having increased branching and/or lateral root development yield by contacting a plant having an endogenous DFD kinase gene operably linked to its native promoter, with a promoter-inducing amount of an agent which induces DFD kinase gene expression, wherein induction of DFD kinase gene expression results in production of a plant having increased branching and/or lateral root development as compared to a plant not contacted with the inducing agent. For example, transcription factors or chemical agents may be used to increase expression of DFD kinase in a plant, in order to provide plants having increased branching for more homogeneous fruit maturation, dwarf varieties, grass with little need of mowing, and the like.

BRIEF DESCRIPTION OF THE DRAWINGS

FIG. 1 shows the nucleotide and deduced amino acid sequences of PINOID (SEQ ID NO:1 and 2, respectively). (See also *Arabidopsis thalia* database, chromosome II BAC T31E10 genomic sequence, Accession No. AC004077.)

Black bars represent coding sequences. Thin line denotes intron.

Figures 2A, 2B:
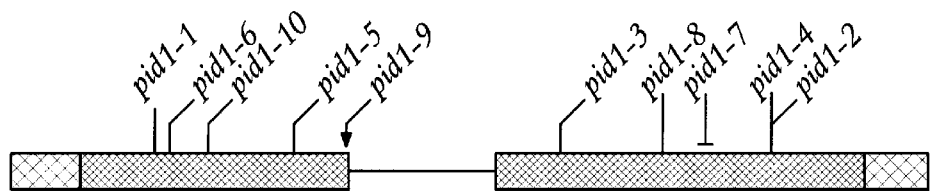
FIG. 2A shows a schematic representation of the PINOID gene and location of ten identified pid mutations. Gray regions represent 5' and 3' untranslated regions.

FIG. 2B illustrates the molecular description of the mutations in 10 mutant PINOID genes depicted in FIG. 2A. Alleles pid1–7 (SEQ ID NO.:3) and pid1–9 (SEQ ID NO.:4) indicate sequences inserted into the relevant PINOID genes.

Figure 3A:
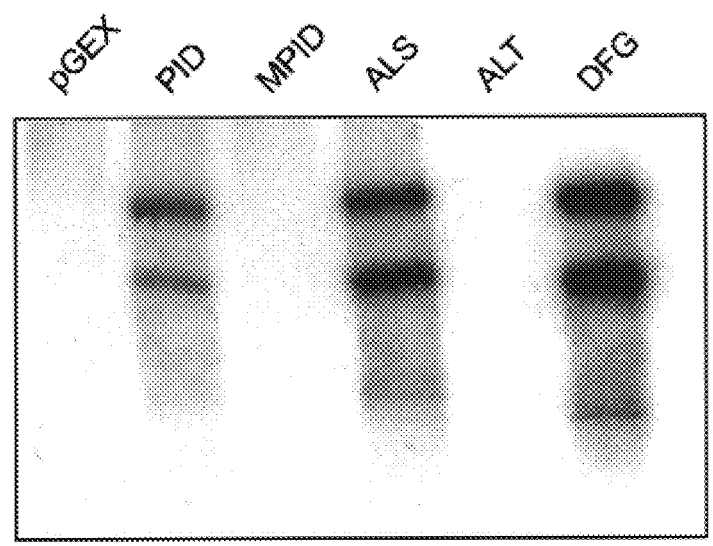
Figure 3B:
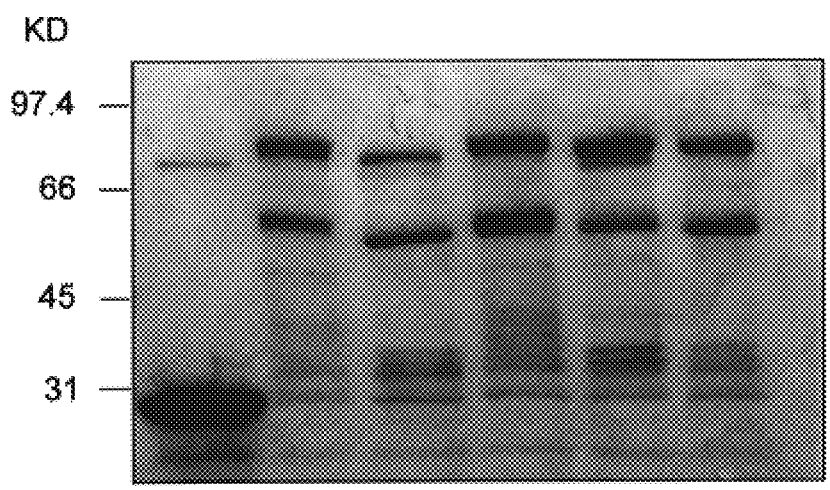

FIGS. 3A and B are photographs of gel assays showing autophosphorylation of the PINOID protein in vitro. FIG. 3A is an autoradiogram of wild type and modified PINOID proteins. pGEX=the bacterial expression vector pGEX-4T-1; PID=wild type PINOID; MPID=D205A; ALS=S288E and S290E; ALT=T285E; DFG=D225G. FIG. 3B is a Coomassie staining of the same gel as shown in FIG. 3A.

Figure 4:
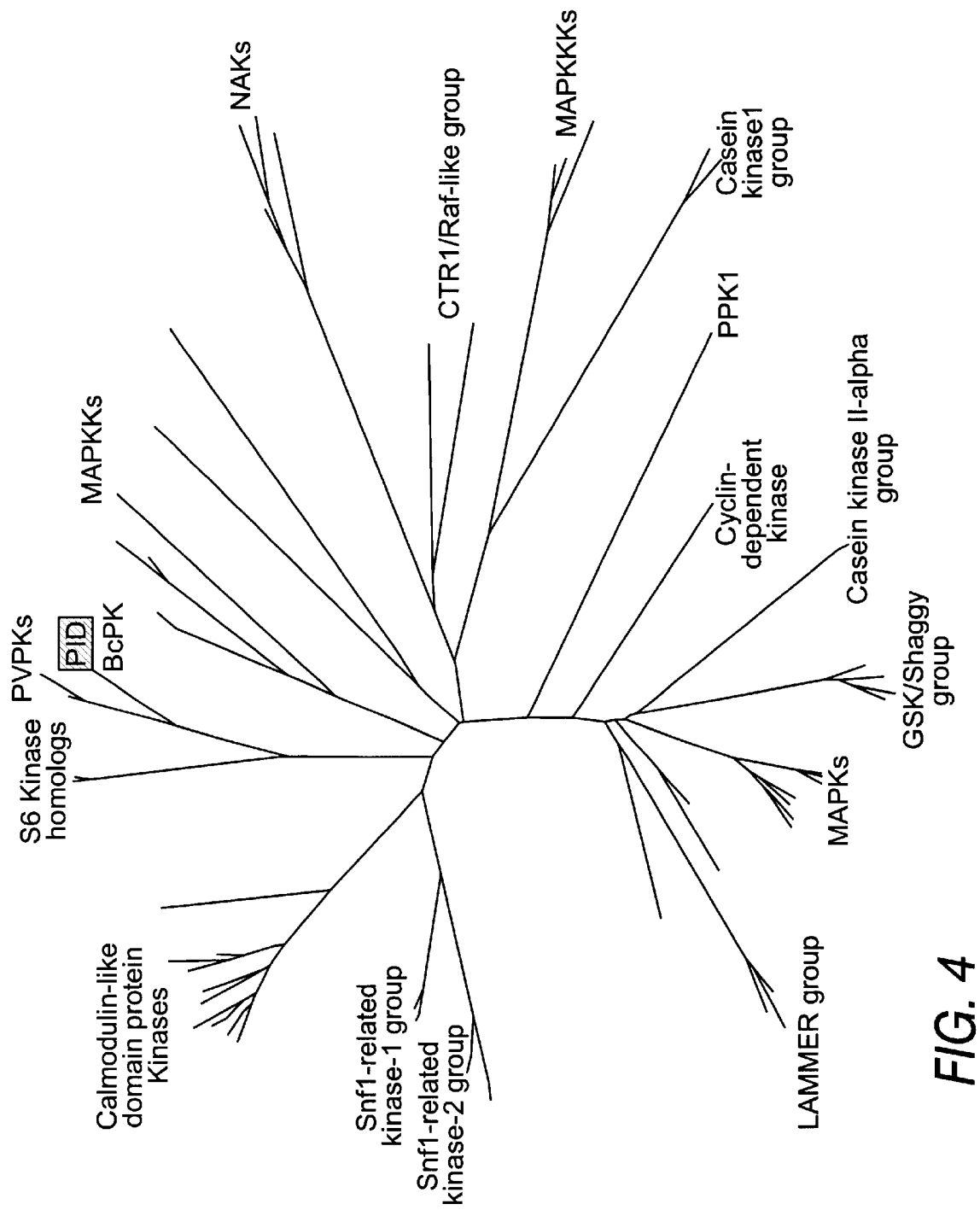

FIG. 4 shows a phylogenetic tree, based on the alignment of protein sequences encoded by the genes shown. Branch lengths reflect evolutionary distance.

FIG. 5 is the deduced amino acid sequence of PID (SEQ ID NO.: 6). Amino acid changes above the sequence indicate residues changed in pid alleles (Table 1), and asterisks indicate residues modified by site-directed mutagenesis in PID expression constructs. Boxes indicate invariant protein kinase residues. The DFD in place of the canonical DFG motif is underlined. A putative regulatory domain is shaded. An arrowhead indicates the location of the single intron. The nucleic acid sequence for pid (SEQ ID NO.: 5) is also shown.

DETAILED DESCRIPTION OF THE INVENTION

In accordance with the disclosed invention, there are provided assays for identifying a new family of plant kinases based on the discovery of a DFD motif. The plant kinase assay includes screening nucleic acid obtained from a plant in order to identify conserved structures characteristic of the newly identified plant kinase family, particularly a contiguous nucleotide sequence or nucleotide sequence that encodes a contiguous DFD amino acid sequence in a region of a putative kinase ordinarily known to encode a "DFG" sequence. The presence of a DFD sequence in the nucleic acid indicates that the nucleic acid encodes a plant kinase, or a fragment thereof.

Based on the identification of the PINOID gene family, a search was conducted to determine whether the DFG=>DFD substitution is a common feature of plant kinases. The search was conducted to locate a similar substitution in other known plant kinases and the results of the search indicated that the DFD locus is a distinguishing characteristic of plant kinases. For example, a BLAST search of Genbank database revealed that NPH, a blue/green light response gene that is auxin controlled, as well as *Brassica rapa* (BcPK) and maize (Sequence AI691652, Ear Tissue cDNA) kinases exhibit a DFG=>DFD substitution in the catalytic domain.

Known methods for locating a particular sequence (e.g., DFD or DNA encoding DFD) as disclosed herein and known in the art can be used in practice of the plant kinase assay described herein. For example, a set of degenerate probes that encode a contiguous DFD amino acid sequence can be used to locate a nucleotide sequence, preferably a complete coding sequence, which encodes a DFD amino acid sequence. Once such a nucleic acid is identified using the plant kinase assay described herein, the corresponding plant kinase can be obtained by expression of the nucleic acid (i.e., preferably comprising a complete coding sequence) so identified, for example, by inserting the nucleic acid into an expression vector as is disclosed herein. Alternatively, putative plant kinase proteins can be sequenced using any known technique to determine the presence of a DFD locus (i.e., a contiguous amino acid sequence of DFD) in the amino acid sequence of the plant protein (e.g., DFD is located beginning at amino acid residue 225 in the PINOID polypeptide described herein (see FIG. 1).

Activity of an enzyme can be determined by measuring the amount of product produced, i.e., the product modified peptide, or the amount of substrate unmodified by the action of the enzyme per unit of time. The measurement of enzyme activity can be performed by separation of the modified and unmodified peptide species using electrophoresis and quantition of the amount of either the residual substrate of the reaction, the product of the reaction, or both. The activity of protein kinases and phosphatases can be determined relative to their ability to modify specific peptide substrates by the addition or removal of modified or unmodified phosphate groups from the peptide substrate.

Typically enzyme activity is determined by incubating the test enzyme with the substrate-modified peptide under optimum conditions known to the art to form product-modified peptides under conditions where the peptide is active. The following general methods are illustrative of different methods for detecting kinase activity.

Many current methods of measuring protein kinase activity are based on the radioactive detection method described by Roskoski (Roskoski, R Jr., (1983) Assays of Protein Kinase Methods in Enzymology 99:3–6; hereby incorporated by reference). A sample containing the kinase of interests is incubated with activators and a substrate in the presence of gamma $^{32}$P-ATP. The substrate can be either a specific protein or peptide fragment or an inexpensive general substrate, such as histone or casein. After the reaction is incubated for suitable period of time, the reaction is stopped and an aliquot of the reaction is placed onto a filter that binds the substrate. The filter is washed to remove excess unincorporated label and the amount of $^{32}$P incorporated into the substrate is measured by scintillation counting. This method is capable of giving accurate measurements of kinase activity in both crude and purified samples.

Use of a modified substrate allows spectrophotometric detection of kinase activity. This method uses the cAMP-dependent protein kinase substrate Kemptide (Bramson et al., (1980) Development of a convenient spectrophotometric assay for peptide phosphorylation catalyzed by adenosine cyclic 3'-5'-monophosphate dependent protein kinase, J. Am. Chem. Soc. 102:7156–7157; hereby incorporated by reference), which has been modified by placing a (o-$NO_2$)-tyrosine residue on the N-terminal side of the phosphorylated serine. This modification doesn't interfere with the peptides ability to be used as a substrate and allows the kinase reaction to be monitored continuously at 430 nm. In contrast, the radioactive method requires that aliquots be taken and the reaction stopped in order to measure incorporation.

A drawback to the spectrophotometric detection methods is that they require large amounts of both the substrate and the kinase being assayed. Therefore these methods may be of limited use when limiting amounts of a novel peptide are being assayed. The spectrophotometric detection method is also not amenable to screening large numbers of samples for relative kinase activity. The final drawback is that a specific peptide is required for each kinase being assayed, and the modifications required to allow detection at 430 nm may have an effect on the recognition of the substrate by the kinase or specificity of the phosphorylation by the kinase.

For these reasons coupled kinase reactions have been developed. One example of this type of reaction is the conversion of phosphoenolpyruvate to pyruvate by phosphotransfer kinase in the presence of ADP (Cook et al (1982) Adenosine cyclic 3'5'-monophosphate dependent protein kinase: Kinetic mechanism for the bovine skeletal muscle catalytic subunit, Biochemistry 21:5794–5799; hereby incorporated by reference). The pyruvate so generated is then converted to lactate by lactate dehydrogenase. The quantity of lactate is determined by reading the absorbence of the reaction at 340 nm. One drawback to this coupled system is that it isn't amenable to being used with crude extracts because any ATPase activity will increase the background. Additionally, the intrinsic oxidative reactions present in such extracts will increase the activity measurements. Furthermore, this type of assay isn't very sensitive.

Another non-radioactive detection method for kinase activity involves alteration of fluorescence upon substrate phosphorylation. A tetradecapeptide derived from the phosphorylation site of the beta subunit of phosphorylase kinase, known as Malantide, is commonly used in this type of assay. Cyclic 3'5' AMP dependent protein kinase phosphorylates the substrate, which then shows a decrease in fluorescence. This assay also allows for continuous monitoring, however, the assay also requires large amounts of the synthetic peptide, as well as a fluorometer.

A variation on the fluorescence methodology uses HPLC to separate non-fluorescently labeled peptide from fluorescently labeled peptide (Seng et al (1991) An HPLC assay for protein kinase activity using fluorescence detection of dansyl peptide substrates, (Abst) The Protein Society: Fifth Symposium, Baltimore Md. June 22–26 p73; hereby incorporated by reference). While this assay doesn't require a large amount of substrate or kinase, it is cumbersome in that each sample must be individually injected and analyzed. Also, the reactions must be stopped before measurement can take place. This method is inappropriate for use with crude samples.

Another fluorescent base kinase activity assay uses peptides that have been modified by the addition of a fluorescent group. U.S. Pat. No 5,120,644, to Ikenaka et al., discloses a method for the measurement of enzymatic activities using the aforementioned peptide substrate and is hereby incorporated by reference. The separation methods use HPLC, hydrophobic chromatography, gel filtration chromatography, ion exchange chromatography, and finally affinity chromatography. This method has several drawbacks including: the samples must be handled several times, the method isn't useful for separating multiple samples at one time, and the researcher must have access to sophisticated chromatographic equipment for the separation of the samples.

One embodiment of the invention provides methods for identifying compounds that modulate the activity of DFD plant kinases. The kinase assays described include incubating at least one putative kinase-modulating compound and a DFD kinase polypeptide containing at least the DFD motif under conditions sufficient for the components to interact, and determining kinase activity in the presence and the absence of the compound, wherein a difference in activity is indicative of a compound that modulates kinase activity of a plant DFD kinase. An exemplary DFD kinase that can be utilized in the method of the invention is a PINOID polypeptide, or fragment thereof, including the substructure containing the DFD domain. Compounds or agents, including small molecules, peptides or nucleic acid sequences, that effect, either increase or decrease, DFD kinase activity by binding to a DFD kinase can be identified by methods described herein. For example, a complex between a DFD kinase and a test compound or agent can be identified and the binding agent isolated therefrom.

Methods for identifying a compound that can modulate DFD-kinase activity are also described. The method includes incubating a DFD kinase, such as PINOID polypeptide or a recombinant cell expressing a PINOID polypeptide or variant thereof and a test compound, under conditions sufficient to allow the components to interact, and measuring the effect of the compound on the activity or expression of the DFD kinase. Compounds that effect DFD kinase activity or gene expression include peptides, polypeptides, peptidomimetics, various small molecules, chemical compounds and biological agents.

The discovery that DFD locus contained in the PINOID polypeptide is a distinguishing characteristic of plant kinases provides the rationale for a method for identifying compounds that modulate plant kinase activity. Compounds or agents that are identified according to the assays described herein can be further evaluated to determine if they also bind to and/or effect DFG kinases. The kinase assays described include incubating at least one compound or agent as described above and a DFG plant kinase polypeptide containing a DFG motif under conditions sufficient for the components to interact, and determining kinase activity in the presence and the absence of the compound, wherein a difference in activity is indicative of a compound that modulates kinase activity of a plant DFG kinase. Those of ordinary skill in the art will readily recognize DFG kinases that can be employed in the present invention. Compounds or agents that are identified to modulate DFD kinases but have no effect on DFG kinases are preferred. Such compounds are extremely useful as potential inhibitors that are specific to plants.

Another embodiment of the described invention provides methods for identifying kinase inhibitors. In this embodiment, the methods comprise incubating at least one putative kinase inhibitor and a DFD kinase, such as a PINOID polypeptide, containing at least the DFD motif under conditions sufficient for the components to interact, separating a complex of the kinase inhibitor and the DFD-containing polypeptide from unbound DFD-containing polypeptide, and isolating the kinase inhibitor from the complex. Preferably, in the complex the kinase inhibitor binds to or complexes with the DFD-containing polypeptide. To confirm that the kinase inhibitor identified by the disclosed methods effectively inhibits the kinase activity of a kinase other than PINOID polypeptide, the disclosed methods may further comprise assaying the autophosphorylating activity of the kinase in the presence and in the absence of the kinase inhibitor identified.

For example, it is believed that certain molecules that block, bind to, complex with or otherwise alter the conformation of the DFD domain in a plant kinase polypeptide will inhibit kinase activity. For example, one of skill in the art could use the exemplary PINOID polypeptide of the invention in order to assess a compound's ability to bind to or block kinase activity in other plant or even in mammalian kinases. Kinase inhibitors identified by this method can be peptides, proteins, such as antibodies that bind to an epitope associated with DFD-containing kinases, or non-proteinaceous small molecules.

As used herein, the term "incubating" comprises conditions that allow contact between a test compound and a DFD kinase polypeptide. "Contacting" comprises in-solution and solid-phase. The test compound may also be a combinatorial library for screening a plurality of compounds. A variety of other agents may be included in the screening assay. These include agents like salts, neutral proteins, e.g., albumin, detergents, etc that are used to facilitate optimal protein-protein binding and/or reduce nonspecific or background interactions. Reagents that improve the efficiency of the assay, such as protease inhibitors, nuclease inhibitors, antimicrobial agents, etc., can also be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Incubations are performed for a suitable period of time, typically between 0.1 and 10 hours will be sufficient.

Polynucleotide sequences encoding DFD motifs can be further evaluated, detected, cloned, sequenced, and the like, either in solution or after binding to a solid support, by any method usually applied to the detection of a specific DNA, such as PCR, oligomer restriction (Saiki et al., 1985, *Bio/Technology*, 3:1008–1012; hereby incorporated by reference), allele-specific oligonucleotide (ASO) probe analysis (Conner et al., 1983, *Proc. Natl. Acad. Sci. USA*, 80:278; hereby incorporated by reference), oligonucleotide ligation assays (OLAs) (Landegren et al., 1988, *Science*, 241:1077; hereby incorporated by reference), and the like. Molecular techniques for DNA analysis have been reviewed (Landegren et al., 1988, *Science*, 242:229–237; hereby incorporated by reference).

Typically, candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate compounds that effect DFD kinase include chemical compounds, peptidomimetics and small molecules. One class is organic molecules, preferably small organic compounds having a molecular weight of more than 50 and less than about 2,500 daltons are of particular interest.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A compound can effect reporter gene expression by either stimulating or inhibiting the expression of the reporter gene. A compound "inhibits" reporter gene expression if the level of transcripts or protein product produced from the reporter gene is decreased as compared with the level in the absence of the test compound. A compound "stimulates" reporter gene expression if the level of transcripts or protein product produced from the reporter gene is increased in the presence of the test compound.

One of ordinary skill in the art can identify a number of reporter genes for use in the screening method of the invention. Examples of reporter genes of use with the invention are lacZ, luciferase, chloramphenicol acetyltransferase, beta-glucuronidase and green fluorescent protein.

The effect of the compound on the reporter gene transcription can be measured by assessing the expression of the reporter by methods well known in the art (e.g., Northern blots; EMSA). Alternatively, the production of protein product from the reporter gene can be measured by methods such as ELISA, RIA, Western blots, SDS-PAGE and other methods well known in the art.

Methods are also described herein for identifying a cellular protein that binds to DFD kinase polypeptide or a variant thereof, by incubating at least one cellular protein and a DFD kinase or PINOID polypeptide or a variant thereof under conditions sufficient for the components to interact, separating a complex of the polypeptide and a putative binding protein from the unbound DFD kinase, and isolating the protein (e.g., similar to a 2-hybrid system).

In a preferred embodiment, an isolated cellular protein is utilized. However, partially purified proteins, fractions of cell extracts, whole cell extracts, or intact cells can be utilized with the described methods. The term "interact" includes in-solution and solid-phase, and includes any complex formation or binding of the cellular component to the kinase polypeptides, including at least the DFD domain, DFD kinases, PINOID or fragments thereof. "Interact" also includes any enzymatic interaction wherein the cellular component performs a biochemical modification of the DFD kinase polypeptide.

Complexes of the cellular components with a kinase polypeptide can be separated from uncomplexed kinase polypeptide by conventional means well known to one of skill in the art. Complex isolation can be accomplished by size separation, physical separation, or other standard methods. For example, nondenaturing gel electrophoresis can be used to separate DFD kinase complexed with a cellular component from uncomplexed DFD kinase.

Once the complex has been isolated, the cellular component can be isolated and characterized by means well known in the art. For example, if the cellular component is a protein, the amino acid sequence of the protein can be determined. A polynucleotide encoding the protein can be produced using DNA synthesis technology. The polynucleotide can then be inserted into a vector and transformed into host cells using molecular biology techniques well known in the art.

Following transformation, large amounts of the protein can be isolated and purified. For example, lysate of transferred cells may be prepared. The protein is then purified for the lysate using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

Another embodiment provides methods for modulating DFD kinase activity. Typically, such a method comprises exposing DFD kinases to compounds or agents identified as described above. As employed herein, the term "modulating" refers to increased or decreased kinase activity, particularly DFD kinase activity. In a preferred embodiment, the identical compounds or agents will modulate DFD kinase activity, but will not or only minimally modulate the activity of DFG kinases. In another embodiment, modulation of DFD kinase activity results in the death of the plant containing the DFD kinase when exposed to such compounds or agents described herein.

In order to determine the phenotypic consequences of PINOID over-expression, the same wild-type and mutant cDNAs described above were cloned into a binary vector and introduced into wild-type plants by Agrobacterium transformation. The T1 generation was selected on antibiotic containing plates and scored for possible over-expression of the PINOID gene. Nine of 170 transgenic plants had a new phenotype. This phenotype was not observed in plants carrying the mutated PINOID construct (0/31). This putative over-expression phenotype was characterized by small dark green plants with a partial loss of apical dominance. In addition, these plants have root defects including an almost complete lack of lateral root formation and aberrant root growth across the surface of the soil, presumably due to loss of agravitropic root growth. As both lateral root formation and the agrivatrophic root response are auxin-dependent processes, it is likely that these phenotypes are caused by over-expression of the PINOID locus.

T1/seeds from the putative PINOID over-expressers were collected, sown on soil and segregation was followed in the T2 generation. The new phenotype segregated as a dominant trait and Northern analysis of total RNA from mutant and non-mutant siblings confirmed that PINOID was over-expressed in the former but not the latter. Significantly, the original PINOID loss-of-function phenotype was detected in the T1 progeny of plants carrying both the wild-type and mutant expression constructs. This indicates that mutant plants are capable of inducing a loss-of-function phenotype, presumably by co-suppression of the endogenous transcript, again confirming the identity of the PINOID kinase.

PINOID Protein

One embodiment described herein provides a substantially pure auxin signaling protein, PINOID (PID). Overexpression of PINOID, in transgenic plants causes such plants to exhibit increased or earlier loss of apical dominance that is characterized by increased branching and/or increased lateral root development as compared with their wild-type counterparts.

Figure 1:
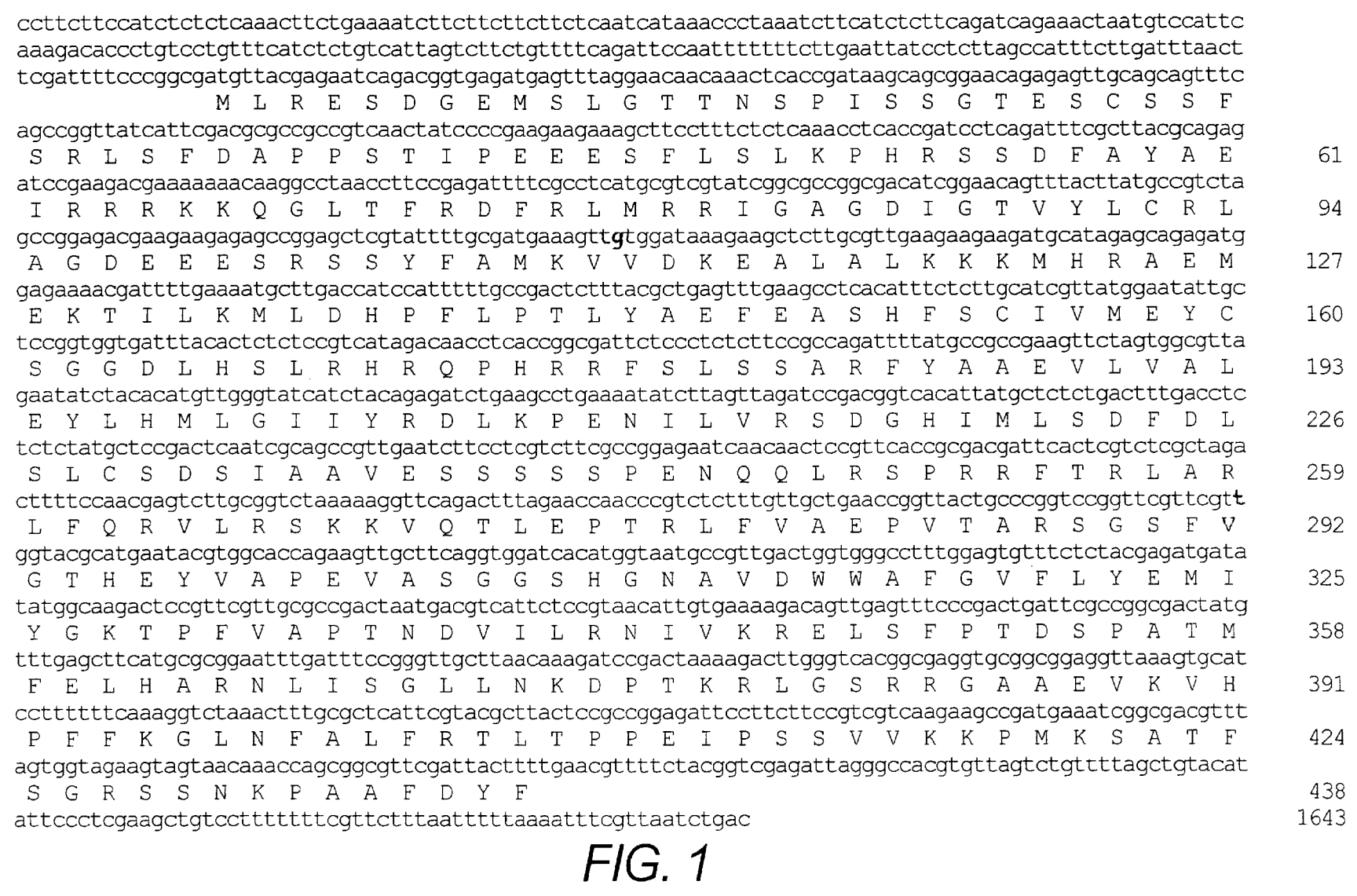

PINOID polypeptide, which is provided herein as an illustrative DFD plant kinase, is exemplified by the amino acid sequence shown in FIG. 1 and SEQ ID NO:2. PINOID polypeptide is characterized as having a predicted molecular weight of approximately 48kD.

Apart from RCN1, which encodes a protein phosphatase (C. Garbers et al, supra), the PINOID polypeptide is so far the only known auxin signaling or response protein that does not seem to be involved in auxin transport and that shows similarity to classic signal transducers, such as the kinases. Moreover, as the biochemistry of kinases is exceedingly well understood (T. Hunter, *Cell* 50:823–29, 1987; hereby incorporated by reference), manipulation of PINOID polypeptide function by mutation of the PINOID gene disclosed herein can be used to create both dominant negative forms and hyperactive forms.

The term "PINOID polypeptide" or PINOID polypeptide family, as used herein means a polypeptide having the amino acid sequence of SEQ ID NO:2, as well as functional fragments thereof, along with other homologous plant kinases, such as the pinoid-like kinase of *Brassica rapa*, BcPK, which has about 88% sequence identity with SEQ ID NO:2 at the amino acid level.

The term "substantially pure" as used herein refers to DFD kinase polypeptide that is substantially free of other proteins, lipids, carbohydrates or other materials with which it is naturally associated. One skilled in the art can purify a DFD kinase using standard techniques for protein purification.

The invention includes functional PINOID polypeptide, and functional fragments thereof. As used herein, the term "functional polypeptide" refers to a polypeptide that possesses biological function or activity which is identified through a functional assay (e.g., kinase activity) and which is associated with a particular biologic, morphologic, or phenotypic alteration in the cell. For example, overexpression of DFD kinase polypeptide results in increased or earlier loss of apical dominance, characterized by increased branching and/or initiation of lateral root development, and the like, e.g., formation of dwarf plants.

The term "functional fragments of DFD polypeptide" refers to all fragments of DFD kinase that retain DFD kinase activity, e.g., auxin signaling or response activity, serine-threonine kinase activity. Biologically functional fragments, for example, can vary in size from a polypeptide fragment as small as an epitope capable of binding an antibody molecule to a large polypeptide capable of participating in the characteristic induction or programming of phenotypic changes within a cell. Functional fragments of DFD kinase include antigenic fragments.

The auxin signaling and/or response activity of DFD kinase can be utilized in bioassays to identify biologically active fragments of DFD kinase polypeptide or related polypeptides. For example, DFD kinase may manipulate auxin signaling in diverse tissues, therefore an assay can be performed to detect DFD kinase auxin signaling activity. Inhibitors of DFD kinase could be used to cause loss of function of DFD kinase resulting in, for example, increased apical dominance characterized by decreased branching and/or decreased lateral root development, and the like.

The polypeptides of the invention also include dominant negative forms of the DFD kinase polypeptide that do not have the biological activity of a DFD kinase. A "dominant negative form" of the DFD kinase is a polypeptide that is structurally similar to DFD kinase but does not have wild-type DFD kinase function. For example, a dominant-negative DFD kinase polypeptide may interfere with wild-type DFD kinase function by binding to, or otherwise sequestering, regulating agents, such as upstream or downstream components, that normally interact functionally with the DFD kinase polypeptide.

As used herein, the term "loss-of-function dominant negative variant" refers to a DFD kinase-encoding polynucleotide wherein the auxin signaling and/or decreased apical dominance activity of DFD kinase has been attenuated sufficiently to cause a decrease in the auxin-signaling and/or decreased apical dominance activity of the DFD kinase polypeptide encoded by the polynucleotide. Such loss-of-function dominant negative variants of the DFD kinase gene are useful for obtaining genetically altered plants according to the methods disclosed herein, for example dwarf plants having loss of apical dominance characterized by decreased branching and/or an increase in apical dominance.

Minor modifications of the DFD kinase primary amino acid sequence may result in proteins which have substantially equivalent activity to the DFD kinase polypeptide described herein in SEQ ID NO:2 (FIG. 1). Such modifications may be deliberate, as by site-directed mutagenesis, or may be spontaneous. All of the polypeptides produced by these modifications are included herein as long as the biological activity of DFD kinase is present, e.g., auxin signaling and/or response activity is present to promote decreased apical dominance characterized by increased branching and/or lateral root growth. Further, deletion of one or more amino acids can also result in a modification of the structure of the resultant molecule without significantly altering its activity. This can lead to the development of a smaller active molecule that could have broader utility. For example, it may be possible to remove amino or carboxy terminal amino acids required for DFD kinase activity.

PINOID polypeptide includes amino acid sequences substantially the same as the sequence set forth in SEQ ID NO:2. The invention includes polypeptides having substantially the same sequence of amino acids as the amino acid sequence set forth in SEQ ID NO:2 or functional fragments thereof, or amino acid sequences that are substantially identical to SEQ ID NO:2. By "substantially the same" or "substantially identical" is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. DFD kinase homologs having substantially the same sequence as DFD kinase can be identified using the phylogenetic tree as shown in FIG. 4. For example, the putative serine/threonine protein kinase (Bcpk1) of *Brassica rapa*, BcPK, has about 88% sequence identity with PINOID at the amino acid level.

Functional fragments include those fragments of DFD kinase that retain the function or activity of DFD kinase, such as the ability to promote auxin signaling or loss of apical dominance. One of skill in the art can screen for the functionality of a fragment by using the examples provided herein, where full-length DFD kinase is described. It is also envisioned that fragments of DFD kinase that inhibit or promote apical dominance can be identified in a similar manner. DFD kinase activity can also be assayed by standard kinase activity assays.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

By a "substantially pure polypeptide" is meant an DFD kinase polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, DFD kinase polypeptide. A substantially pure DFD kinase polypeptide may be obtained, for example, by extraction from a natural source (e.g., a plant cell); by expression of a recombinant nucleic acid encoding an DFD kinase polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

The invention provides polynucleotides encoding the DFD kinase protein. These polynucleotides include DNA, cDNA and RNA sequences that encode DFD kinase. It is understood that all polynucleotides encoding DFD kinase are also included herein, as long as they encode a polypeptide with DFD kinase activity. Such polynucleotides include naturally occurring, synthetic, and intentionally manipulated polynucleotides. For example, DFD kinase polynucleotide may be subjected to site-directed mutagenesis. The polynucleotide sequence for DFD kinase also includes antisense sequences, sequences encoding dominant negative forms of DFD kinase, and sequences encoding DFD kinase fragments or peptides. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of DFD kinase polypeptide encoded by the nucleotide sequence is functionally unchanged.

Specifically disclosed herein is a polynucleotide sequence containing the PINOID gene. Preferably, the PINOID nucleotide sequence is the sequence set forth in SEQ ID NO:1. The term "polynucleotide" or "nucleic acid sequence" refers to a polymeric form of nucleotides at least 10 bases in length. By "isolated polynucleotide" or "purified polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA. It also includes a recombinant DNA that is part of a hybrid gene encoding additional polypeptide sequence.

An isolated polynucleotide sequence encoding a polypeptide having the amino acid sequence of SEQ ID NO:2 is also provided by the teachings described herein. The PINOID transcript contains a single, long open reading frame that encodes an approximately 438-amino acid protein.

A polynucleotide encoding a DFD kinase comprises the nucleotide sequence in FIG. 1 (SEQ ID NO:1), as well as nucleic acid sequences complementary to that sequence. A complementary sequence may include an antisense nucleotide. When the sequence is RNA, the deoxyribonucleotides A, G, C, and T of FIG. 1C are replaced by ribonucleotides A, G, C, and U, respectively. A polynucleotide encoding a DFD further comprises fragments ("probes") of the above-described nucleic acid sequences that are at least 15 bases in length, which is sufficient to permit the probe to selectively hybridize to DNA that encodes the protein of FIG. 1 (SEQ ID NO: 2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated DFD kinase nucleotide sequences.

Specifically disclosed herein is a cDNA sequence for DFD kinase, PINOID. FIG. 1 shows the complete cDNA and deduced protein sequences (SEQ ID NO:1 and 2, respectively).

A "substantially identical" nucleic acid sequence codes for a substantially identical amino acid sequence as defined above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

A polynucleotide sequence encoding a DFD kinase polypeptide comprises nucleotide sequences encoding the disclosed sequence (e.g., SEQ ID NO:2) and conservative variations thereof The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences encoding DFD kinase can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the DFD kinase polynucleotide sequences may be inserted into an expression vector. The term "expression vector" refers to a plasmid, virus or other vehicle known in the art that has been manipulated by insertion or incorporation of the DFD kinase genetic sequences. Polynucleotide sequence that encodes DFD kinase can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included in the invention (see e.g., Bitter et al., 1987, Methods in Enzymology 153:516–544). The expression of structural genes employed in the present invention may be driven by a number of promoters. Although the endogenous promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., *Nature,* 310:511, 1984; Odell, et al., *Nature,* 313:810, 1985); the full-length transcript promoter from Figwort Mosaic Virus (FMV) (Gowda, et al., *J. Cell Biochem.,* 13D: 301, 1989) and the coat protein promoter of TMV (Takamatsu, et al., EMBO J. 6:307, 1987). Alternatively, plant promoters such as the light-inducible promoter from the small subunit of ribulose bis-phosphate carboxylase (ssRUBISCO) (Coruzzi, et al., *EMBO J.,* 3:1671, 1984; Broglie, et al., *Science,* 224:838, 1984); mannopine synthase promoter (Velten, et al., EMBO J., 3:2723, 1984), nopaline synthase (NOS) and octopine synthase (OCS) promoters (carried on tumor-inducing plasmids of *Agrobacterium tumefaciens* and have plant activity); ethylene inducible promoter whose level of activity is increased in response to treatment with ethylene or an equivalent compound such as propylene; heat shock promoters, e.g., soybean hspl7.5-E or hspl 7.3-B (Gurley, et al., *Mol. Cell. Biol.,* 6:559, 1986; Severin, et al., *Plant Mol. Biol.,* 15:827, 1990); or ethanol-inducible promoters (Caddick et al., *Nature Biotech.,* 16:177, 1998) may be used.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.,* 90:4567, 1993); In2-1 and In2-2 regulator sequences which are activated by substituted benzenesulfonamides, e.g., herbicide safeners (Hershey, et al., *Plant Mol. Biol.,* 17:679, 1991); the GRE regulatory sequences which are induced by glucocorticoids (Schena, et al., *Proc. Natl. Acad. Sci., USA.,* 88:10421, 1991); and ethanol-inducible promoters (Caddick et al., supra). Those of skill in the art will know other promoters, both constitutive and inducible, and enhancers.

The particular promoter selected should be capable of causing sufficient expression to result in the production of an effective amount of the structural gene product, e.g., DFD kinase, to cause auxin signaling or loss of apical dominance as characterized by increased branching and/or lateral root development or antisense to cause increased apical dominance, as compared with wild type plant. The promoters used in the vector constructs of the present invention may be modified, if desired, to affect their control characteristics. Tissue specific promoters may also be utilized in the present invention. As used herein, the term "tissue-specific promoter" means a DNA sequence that serves as a promoter, i.e., regulates expression of a selected DNA sequence operably linked to the promoter. A tissue-specific promoter effects expression of the selected DNA sequence in specific cells, e.g., in the root or in the shoot of a plant. The term also covers so-called "leaky" promoters, which regulate expression of a selected DNA primarily in one tissue, but cause expression in other tissues as well. Such promoters also may include additional DNA sequences that are necessary for expression, such as introns and enhancer sequences. An example of a tissue specific promoter is the HHA promoter expressed in shoot meristems (Atanassova, et al., *Plant J.*, 2:291, 1992). Other tissue specific promoters useful in transgenic plants, including the cdc2a promoter and cyc07 promoter, will be known to those of skill in the art. (See for example, Ito, et al., *Plant Mol. Biol.*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993). Examples of tissue specific promoters active in floral meristems are the promoters of the apetala 3 and apetala 1 genes which are described in Jack et al., *Cell*, 76:703, 1994 and Hempel et al., *Development*, 124:3845, 1997. In addition, meristem-specific promoter from the UFO gene is included (U.S. Pat. No. 5,880,330).

Optionally, a selectable marker may be associated with the heterologous nucleic acid sequence, i.e., the structural gene operably linked to a promoter. As used herein, the term "marker" refers to a gene encoding a trait or a phenotype that permits the selection of, or the screening for, a plant or plant cell containing the marker. The marker gene may be an antibiotic resistance gene whereby the appropriate antibiotic can be used to select for transformed cells from among cells that are not transformed or the marker gene may be herbicide resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). Those of skill in the art will know other suitable markers that can be employed in the present invention.

Vector(s) employed in the present invention for transformation of a plant cell to modulate apical dominance comprise a nucleic acid sequence comprising at least one structural gene encoding a protein that modulates apical dominance, operably associated with a promoter. To commence a transformation process in accordance with the present invention, it is first necessary to construct a suitable vector and properly introduce it into the plant cell. The details of the construction of the vectors then utilized herein are known to those skilled in the art of plant genetic engineering. In the present invention, the gene encoding a protein that modulates apical dominance is preferably a gene encoding a kinase containing the DFD catalytic domain. The DFD kinase gene may be utilized alone or in combination with another structural gene, such as another gene which encodes a protein important in auxin signaling or control of apical dominance. Examples of such genes include Arabadopsis AUX1, regulatory subunit A, AXR1, AUX/IAA gene family, DOC, PIN, PIN 2, PINFORMED, TIR1, and the like, and combinations thereof.

For example, the heterologous nucleic acid sequences utilized in the present invention can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science*, 227:1229, 1985, both incorporated herein by reference).

One of skill in the art will be able to select an appropriate vector for introducing the heterologous nucleic acid sequence in a relatively intact state. Thus, any vector that will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology*, Vol. 153, 1987, Wu and Grossman, Eds., Academic Press, incorporated herein by reference). As used herein, the term "transformation" means alteration of the genotype of a host plant by the introduction of a heterologous nucleic acid sequence. "Transformation" refers to the insertion of an exogenous polynucleotide into a host cell, irrespective of the method used for the insertion, for example, direct uptake, transduction, bombardment or electroporation. The exogenous polynucleotide may be maintained as a non-integrated vector, for example, a plasmid, or alternatively, may be integrated into the host genome.

One approach, known as direct transformation, induces uptake and integration of plasmid or linearized DNA in the genome of plant protoplasts, i.e., single cells stripped of cell wall material (Lorz et al., 1985, *Mol. Genet.* 199:178–182). Another approach involves the transfer of exogenous bacteriophage or plasmid DNA into germinating pollen grains to modify plant properties. As the pollen tube emerges from the mature pollen grain, cell wall material is deposited behind the growing tip.

A third approach relies on infection by Agrobacterium bacterium, which inserts sequences of a plasmid, known as the Ti-plasmid, into the genome of plant cells (Chilton et al., 1977, *Cell* 11:263:271). A heterologous nucleic acid sequence can be introduced into a plant cell utilizing *Agrobacterium tumefaciens* containing the Ti plasmid. In using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology*, 1:262, 1983; Hoekema, et al., *Nature*, 303:179, 1983). Such a binary system is preferred because it does not require integration into Ti plasmid in Agrobacterium.

Methods involving the use of Agrobacterium include, but are not limited to: 1 co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in situ transformation by Agrobacterium, as described by Bechtold, et al., (*C. R. Acad. Sci. Paris*, 316:1194, 1993). This approach is based on the vacuum infiltration of a suspension of Agrobacterium cells.

The preferred method of introducing heterologous nucleic acid into plant cells is to infect such plant cells, an explant, a meristem or a seed, with transformed *Agrobacterium tumefaciens* as described above. Under appropriate conditions known to those skilled in the art, the transformed plant cells are grown to form shoots, roots, and develop further into plants.

A preferred vector(s) of the invention comprises a Ti plasmid binary system wherein the heterologous nucleic acid sequence encodes a DFD kinase protein. Such a vector may optionally contain at least one other nucleic acid sequence which encodes a second factor or protein active in auxin signaling or control of apical dominance, such as Arabadopsis AUX1, regulatory subunit A, AXR1, AUX/IAA, DOC1, PIN, PIN 2, PINFORMED, TIR1 and combinations thereof. Alternatively, two vectors can be utilized wherein each vector contains at least one heterologous nucleic acid sequence. Other plant architecture development genes can be utilized for construction of one or more vectors, in a similar manner.

Alternatively, heterologous nucleic acid can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

Heterologous nucleic acid can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., Nature 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). CaMV viral DNA genome is inserted into a parent bacterial plasmid creating a recombinant DNA molecule that can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants. Methods are also known for use of Tobacco mosaic virus as a vector to obtain expression of recombinant DNA (U.S. Pat. No. 5,955,647).

Methods for Producing Genetically Modified Plants

In another embodiment, the invention provides a method for genetically modifying a plant cell such that a plant, produced from the cell, is characterized as having modulated apical dominance. Modulated apical dominance includes a change in branching and/or lateral root development as compared with a wild type plant. The method includes introducing at least DFD kinase encoding polynucleotide of the invention into a plant cell to obtain a transformed plant cell and growing the transformed plant cell under conditions that permit expression of DFD kinase polypeptide, thereby producing a plant having modulated apical development. The term "modulated", as employed with respect to the present invention, refers to increased apical development or inhibited apical development as compared with a wild-type plant.

Decreased apical dominance can be achieved by induction or augmentation of DFD kinase gene expression or DFD kinase polypeptide activity. Vectors encoding DFD kinase polypeptide that are useful in the method of the invention are described herein. For example, DFD kinase gene expression under control of an inducible promoter or constitutive promoter can be used to increase DFD kinase expression over levels found in wild-type plants.

Similarly, increased apical dominance can be achieved by inhibiting DFD kinase gene expression or DFD kinase polypeptide activity in the plant. DFD kinase antisense or DFD kinase dominant negative nucleic acid sequences can be used to inhibit DFD kinase gene expression or decrease wild-type DFD kinase protein activity, respectively, for example.

While the present examples demonstrate that constitutive expression of a gene (e.g., PINOID) causes loss of apical dominance, and that expression of an antisense nucleic acid can be used to increase apical dominance or delay loss of apical dominance, this system could be modified such that branching and/or lateral root development would be increased using dominant negative polypeptides. For example, dominant-negative versions of DFD kinase and/or other apical dominance or auxin signaling regulatory genes could be expressed constitutively. Dominant-negative mutants are proteins that actively interfere with the function of a normal, endogenous protein. Thus, the action of a gene can be blocked without inactivating the structural gene itself or its RNA. This strategy has been successful for both signal transduction molecules and for transcription factors (e.g., Attardi, et al., Proc. Natl. Acad. Sci. USA, 90:10563, 1993; Lloyd, et al., Nature, 352:635, 1991; Logeat, et al., EMBO J., 10:1827, 1991: Mantovani, et al., J. Biol. Chem., 269:20340, 1994; Ransone, et al., Proc. Natl. Acad. Sci. USA, 87:3806, 1990; Richardson, et al., Mech. Dev., 45:173, 1994; Tsai, et al., Genes Dev., 6:2258, 1992; Thomas et al., Nature Genetics, 17:58, 1997; Wittbrodt, J. And Rosa, F., Genes and Development, 8:1448, 1994; Kashles et al., Mol. Cell. Biol., 11:1454, 1991; Pierce & Kimelman, Development, 121:755, 1995).

In another embodiment, the invention includes a method of producing a genetically modified plant characterized as having modulated auxin signaling, including contacting a plant cell with a vector, including a heterologous nucleic acid sequence comprising at least one structural gene encoding DFD kinase polypeptide, operably associated with a promoter to obtain a transformed plant cell; producing a plant from the transformed plant cell; and selecting a plant exhibiting early loss of or decreased apical dominance.

In yet another embodiment, there are provided plants and methods for genetically modifying a plant expressing DFG kinases, preferably kinases having replaced the DFD domain with the DFG domain. Those of skill in the art will readily recognize methods that can be employed to replace, transform or mutate a DFD domain to a DFG domain. Plants of the present invention can either express no or minimal levels of endogenous DFD kinases, having been replaced with kinases containing the DFG domain, or can express normal levels of DFD kinases supplemented with kinases containing the DFG domain. Such plants typically will be tolerant/resistant to compounds which bind/inhibit DFD domains but not DFG domains, such as antibodies specific to the DFD domain.

As used herein, the term "contacting" refers to any means of introducing the vector(s) into the plant cell, including chemical and physical means as described above. Preferably, contacting refers to introducing the nucleic acid or vector into plant cells (including an explant, a meristem or a seed), via Agrobacterium tumefaciens transformed with the heterologous nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part). Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al., Science, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g. early loss of apical dominance.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting modulated apical dominance can be selected by visual observation. The invention includes a plant produced by the method of the invention, including plant tissue, seeds, and other plant cells derived from the genetically modified plant.

In yet another embodiment, the invention provides a method for modulating auxin signaling in a plant cell including contacting a plant cell with a vector as described above to obtain a transformed plant cell, growing the transformed plant cell under plant forming conditions, and modulating auxin signaling in the plant. The method of the invention requires that the promoter sequence operably linked with the structural gene. The promoter is an inducible promoter when induction of auxin signaling is desired. For example, when a plant cell and plant is produced as described above, contacting the promoter, linked with a nucleic acid sequence encoding a DFD kinase, with an appropriate inducer, induces modulated auxin signaling. Such inducible promoters are described above, and include those promoters preferably inducible by chemical means.

By "transformation" is meant a generic change induce in a cell following incorporation of new DNA (i.e. DNA exogenous to the cell). Where the cell is a mammalian cell, the genetic change is generally achieved by introduction of the DNA into the genome of the cell (i.e. stable). By "transformed cell" is meant a cell into which (or into an ancestor of which) has been introduced, by means of recombinant DNA techniques, a DNA molecule encoding DFD kinase. Transformation of a host cell with recombinant DNA may be carried out by conventional techniques as are well known to those skilled in the art.

Antibodies

The DFD kinase polypeptides of the invention can be used to produce antibodies that are immunoreactive or bind to epitopes of the DFD kinase polypeptides, preferably antibodies that are do not bind or are not specific for DFG domains. Antibodies that consist essentially of pooled monoclonal antibodies with different epitopic specificities, as well as distinct monoclonal antibody preparations are provided.

The preparation of polyclonal antibodies is well-known to those skilled in the art. See, for example, Green et al., Production of Polyclonal Antisera, in: *Immunochemical Protocols* (Manson, ed.), pages 1–5 (Humana Press 1992); Coligan et al., Production of Polyclonal Antisera in Rabbits, Rats, Mice and Hamsters, in: *Current Protocols in Immunology*, section 2.4.1 (1992), which are hereby incorporated by reference.

The preparation of monoclonal antibodies likewise is conventional. See, for example, Kohler & Milstein, 1975, Nature 256:495; Coligan et al., sections 2.5.1–2.6.7; and Harlow et al., in: *Antibodies: a Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Bames et al., Purification of Immunoglobulin G (IgG), in: *Methods in Molecular Biology*, Vol. 10, pages 79–104 (Humana Press 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment that contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., 1960, Arch. Biochem. Biophys. 89:230, Porter, 1959, Biochem. J. 73:119; Edelman et al., 1967, *Methods in Enzymology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of V$_H$ and V$_L$ chains. This association may be noncovalent, as described in Inbar et al., 1972, Proc. Nat'l Acad. Sci. USA 69:2659. Alternatively, the variable chains can be linked by an intermolecular disulfide bond or cross-linked by chemicals such as glutaraldehyde. See, e.g., Sandhu, supra. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., 1991, *Methods: a Companion to Methods in Enzymology*, Vol. 2, page 97; Bird et al., 1988, Science 242:423–426; Ladner et al., U.S. Pat. No. 4,946,778; Pack et al., 1993, Bio/Technology 11:1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106 (1991).

Antibodies that bind to the DFD kinase polypeptide of the invention can be prepared using an intact polypeptide or fragments containing small peptides of interest as the immunizing antigen. The polypeptide or a peptide used to immunize an animal can be derived from translated cDNA or chemical synthesis that can be conjugated to a carrier protein, if desired. Such commonly used carriers that are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

Genetically Modified Plants

In one embodiment, the invention provides a genetically modified plant comprising at least one heterologous nucleic acid sequence encoding DFD kinase in its genome, wherein the DFD kinase sequence modulates apical dominance in the plant. The plant is therefore characterized as having modulated apical dominance. Also included herein are plant cells and plant tissue, all derived from the genetically modified plant of the invention. In addition, seeds that can germinate into a genetically modified plant as described herein are also provided.

In yet another embodiment, the invention provides a genetically modified plant comprising at least one heterologous nucleic acid sequence encoding DFD kinase in its genome, wherein the DFD domain has been replaced with the DFG domain. Also included herein are plant cells and plant tissue, all derived from the genetically modified plant of the invention. In addition, seeds that can germinate into a genetically modified plant as described herein are also provided.

The term "genetic modification" as used herein refers to the introduction of one or more heterologous nucleic acid sequences into one or more plant cells, which can generate whole, sexually competent, viable plants. The term "genetically modified" as used herein refers to a plant that has been generated through one of the aforementioned processes. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete-producing cells, and cells which regenerate into whole plants. Accordingly, a seed comprising multiple plant cells capable of regenerating into a whole plant is included in the definition of "plant cell".

As used herein, the term "plant" refers to a whole plant, a plant part, a plant cell, or a group of plant cells, such as plant tissue, for example. Plantlets are also included within the meaning of "plant". Plants included in the invention are any plants amenable to transformation techniques, including monocotyledonous and dicotyledonous plants, as well as conifers, and the like.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or Brassica oleracea (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, cottonwood, sweetgum, acacia, oak, and the like. DFD kinase loss-of-function dominant negative mutants in such woody species produce trees having fewer lateral branches and, hence, a reduced number of knots in lumber produced from such genetically engineered species.

The term "heterologous nucleic acid sequence" as used herein refers to at least one structural gene operably associated with a regulatory sequence such as a promoter. The nucleic acid sequence originates in a foreign species, or, in the same species if substantially modified from its original form. For example, the term "heterologous nucleic acid sequence" includes a nucleic acid originating in the same species, where such sequence is operably linked to a promoter that differs from the natural or wild-type promoter.

As used herein, the term "nucleic acid sequence" refers to a polymer of deoxyribonucleotides or ribonucleotides, in the form of a separate fragment or as a component of a larger construct. DNA encoding the proteins utilized in the method of the invention can be assembled from cDNA fragments or from oligonucleotides that provide a synthetic gene that is capable of being expressed in a recombinant transcriptional unit. Polynucleotide or nucleic acid sequences of the invention include DNA, RNA and cDNA sequences (see description previously).

Antisense Polynucleotides

Inhibition of or delayed loss of apical dominance or increased apical dominance can be achieved by introduction of antisense molecules into a plant cell from which a transformed or genetically modified plant is produced. This approach also includes, for example, antisense nucleic acid, ribozymes, or triplex agents to block transcription or translation of DFD kinase mRNA, either by masking that mRNA with an antisense nucleic acid or triplex agent, or by cleaving it with a ribozyme. An exemplary antisense polynucleotide of the invention is set forth in SEQ ID NO:3 (FIG. 2).

In one embodiment, the invention includes a genetically modified plant having a transgene disrupting or interfering with expression of DFD kinase gene (DFD kinase), chromosomally integrated into the genome of the plant. A "transgene" is any piece of DNA that is inserted by artifice into a cell, and becomes part of the genome of the organism or plant that develops from that cell. Such a transgene may include a gene that is partly or entirely heterologous (i.e., foreign) to the transgenic organism, or may represent a gene homologous to an endogenous gene of the organism. As used herein, the term "transgene" means a DNA sequence that includes one or more selected DNAs to be expressed in a genetically modified or transgenic plant which is partly or entirely heterologous, i.e., foreign, to the transgenic plant, or homologous to an endogenous gene of the transgenic plant, but which is designed to be inserted into the plant's genome at a location which differs from that of the natural gene. A transgene includes one or more promoters and any other DNA, such as introns, necessary for expression of the selected DNA, all operably linked to the selected DNA, and may include an enhancer sequence.

The invention includes a method of producing a genetically modified plant characterized as having early or increased loss of apical dominance by contacting a plant cell with a vector containing a nucleic acid sequence including at least a structural gene disrupting or interfering with expression of DFD kinase polypeptide, wherein the gene is operably associated with a promoter, to obtain a transformed plant cell; producing a plant from the transformed plant cells; and selecting a plant exhibiting early or increased loss of apical dominance as characterized by early release of lateral branches from growth inhibition. Loss of apical dominance can be identified as demonstrated in the Examples herein, e.g., visual observation of transgenic plant branching and lateral root development versus wild-type plant branching and lateral root development. The time for loss of apical dominance can be determined by counting the number of branching shoots produced by a plant. Hormonal regulation of apical dominance is described in Iatamos et al., *Plant Hormones*, Edited by J. J. Davies (1995), pp 572–597.

The method of producing a genetically modified plant characterized as having delayed loss of apical dominance includes contacting a plant cell with a vector containing an DFD kinase antisense nucleic acid sequence or a nucleic acid sequence encoding a dominant negative form of DFD kinase, operably associated with a promoter.

Antisense nucleic acids are DNA or RNA molecules that are complementary to at least a portion of a specific mRNA molecule (Weintraub, 1990, Scientific American, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target DFD kinase-producing cell. The use of antisense methods to inhibit the in vitro translation of genes is well known in the art (Marcus-Sakura, 1988, Anal. Biochem., 172:289). Virus can also be used for antisense suppression (Angell and Balcombe, *Embo J.*, 16:3675, 1997).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1(3):227; Helene, C., 1991, Anticancer Drug Design, 6(6):569).

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences in an RNA molecule and cleave it (Cech, 1988, J. Amer. Med. Assn., 260:3030). A major advantage of this approach is that, because they are sequence-specific, only mRNAs with particular sequences are inactivated.

There are two basic types of ribozymes namely, tetrahymena-type (Hasselhoff, 1988, Nature, 334:585) and "hammerhead"-type. Tetrahymena-type ribozymes recognize sequences that are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Dominant Negative Mutations

In another embodiment of the present invention, a nucleotide sequence encoding a DFD kinase dominant negative protein is provided. For example, genetic constructs that contain such a dominant negative encoding gene may be operably linked to a promoter, such as a tissue-specific promoter. Examples of such promoters and methods of use are described above.

Such constructs are useful in methods of modulating loss of apical dominance or controlling onset of branching and lateral root development in a plant. For example, a method of the invention includes transforming a plant cell or tissue with a genetic construct encoding a dominant negative DFD kinase protein and suitable promoter in operable linkage and expressing the dominant negative encoding DFD kinase gene, thereby modulating loss of apical dominance by interfering with wild-type DFD kinase activity.

Screen for DFD Kinase Agonists or Antagonists

In another embodiment, the invention provides a method for identifying a compound that modulates DFD kinase protein activity or gene expression. The method includes incubating components comprising the compound, DFD kinase polypeptide or a recombinant cell expressing DFD kinase polypeptide, under conditions sufficient to allow the components to interact and determining the effect of the compound on DFD kinase activity or expression. The effect of the compound on DFD kinase activity can be measured by a number of assays, and may include measurements before and after incubating in the presence of the compound. Compounds that affect DFD kinase activity or gene expression include peptides, peptidomimetics, polypeptides, chemical compounds and biologic agents. Assays include Northern blot analysis of DFD kinase mRNA (e.g., for gene expression) and Western blot analysis (e.g., for protein activity).

In yet another embodiment, the invention method further comprises evaluating for identifying a compound that specifically modulates DFD kinase protein activity or gene expression. The method includes incubating components comprising the compounds identified above, DFG kinase polypeptide or a recombinant cell expressing DFG kinase polypeptide, under conditions sufficient to allow the components to interact and determining the effect of the compound on DFG kinase activity or expression. The effect of the compound on DFG kinase activity can be measured by a number of assays, and may include measurements before and after incubating in the presence of the compound. Compounds that affect DFG kinase activity or gene expression include peptides, peptidomimetics, polypeptides, chemical compounds and biologic agents. Assays include Northern blot analysis of DFG kinase mRNA (e.g., for gene expression) and Western blot analysis (e.g., for protein activity).

Incubating includes conditions that allow contact between the test compound and DFD kinase polypeptide or with a recombinant cell expressing DFD kinase polypeptide. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete-producing cells, and cells which regenerate into whole plants. Accordingly, a seed comprising multiple plant cells capable of regenerating into a whole plant is included in the definition of "plant cell".

Alternatively, DFD kinase encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

DFD kinase nucleic acid sequences can also be introduced into plant cells by electroporation (Fromm, et al., *Proc. Natl. Acad. Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing DFD kinase nucleic acid into a plant cell is high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3–16, 1991) and Klein, et al. (*Bio/Techniques* 10:286, 1992). Although, typically only a single introduction of a new nucleic acid sequence is required, this method particularly provides for multiple introductions.

As used herein, the term "contacting" refers to any means of introducing DFD kinase into the plant cell, including chemical and physical means as described above. Preferably, contacting refers to introducing the nucleic acid or vector into plant cells (including an explant, a meristem or a seed), via *Agrobacterium tumefaciens* transformed with the DFD kinase encoding nucleic acid as described above.

Screen for Identifying Novel Auxin-Signaling and/or Response Genes

The invention provides a method of identifying novel auxin-signaling and/or response genes related to DFD kinase by probing a nucleic acid library with at least a fragment of an isolated polynucleotide encoding DFD kinase, and selecting those clones that hybridize with the fragment. Novel auxin resistance genes, such as homologs of DFD kinase are identified by any of a number of methods. The nucleotide sequence encoding a novel auxin response gene can be isolated according to any one of a variety of methods well known to those of ordinary skill in the art. For example, DNA encoding a DFD kinase homolog can be isolated from either a cDNA library or from a genomic DNA library (see, e.g., Sambrook et al., 1989. *Molecular Cloning: A Laboratory Manual,* 2nd Ed., Cold Spring Harbor Laboratory Press, Cold Spring Harbor, N.Y.). In one embodiment, a fragment of a polynucleotide encoding DFD kinase may be used as a hybridization probe with a cDNA library from the target organism of interest, where low stringency conditions are used. The probe may be a large fragment, or one or more short degenerate primers. In a preferred embodiment, the probe is at least eight nucleotides in length.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under more stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g., plant species, primate species, particularly human; rodents, such as rats and mice, canines, felines, bovines, ovines, equines, yeast, and nematodes.

Alternatively, the DNA encoding a novel auxin-signaling and/or response gene can be isolated using standard polymerase chain reaction (PCR) amplification of synthetic oligonucleotide primers, e.g., as described in Mullis et al., U.S. Pat. No. 4,800,159, or expression cloning methods well known in the art (see, e.g., Sambrook et al., 1989, *Molecular Cloning: A Laboratory Manual,* 2nd Ed., Cold Spring Harbor Laboratory Press, Cold Spring Harbor, N.Y.). One of skill in the art can readily design primers for PCR amplification based on the sequence of a polynucleotide encoding DFD kinase polypeptide.

Yet another alternative method for identifying homologous or related genes utilizes the so-called "two-hybrid" system of Fields & Song described in U.S. Pat. No. 5,283,173. The two-hybrid system involves the use of two chimeric genes that encode hybrid proteins to test for an interaction between a known protein and protein of interest. The first chimeric gene codes for a DFD kinase polypeptide, or functional fragment thereof, fused to the DNA-binding domain of a transcriptional activator. The second chimeric gene codes for a protein of interest fused to the transcriptional activation domain of the transcriptional activator. Alternatively, the protein of interest may not be known and could be derived, for example, from a cDNA library. In a suitable host cell such as yeast, if the protein of interest and the bait protein do interact they bring into proximity the DNA-binding and transcriptional activation domains. This proximity is sufficient to cause transcription of a marker gene placed under the control of a promoter containing a binding site for the DNA-binding domain. Thus, the two-hybrid system generally allows detection of an interaction between two proteins by means of the positive signal of expression of a reporter gene.

Between plant species, e.g. monocotyledons, dicotyledons, and woody species, homologs typically have substantial sequence similarity, i.e. at least 75% sequence identity between nucleotide sequences. Sequence similarity is calculated based on a reference sequence, which may be a subset of a larger sequence, such as a conserved motif, coding region, or flanking region, for example. A reference sequence will usually be at least about 18 nucleotides (nt) long, more usually at least about 30 nt long, and may extend to the complete sequence that is being compared. Algorithms for sequence analysis are known in the art, such as BLAST, described in Altschul et al. (1990) *J. Mol. Biol.* 215:403–10. The sequences provided herein are essential for recognizing DFD kinase related and homologous proteins in database searches.

A "susceptible plant" refers to a plant that can be induced to utilize its endogenous DFD kinase gene to achieve early or increased loss of apical dominance. The term "promoter inducing amount" refers to that amount of an agent necessary to elevate DFD kinase gene expression above DFD kinase expression in a plant cell not contacted with the agent. For example, a transcription factor or a chemical agent may be used to elevate gene expression from DFD kinase native promoter, thus inducing the promoter and DFD kinase gene expression.

The above disclosure generally describes the present invention. A more complete understanding can be obtained by reference to the following specific examples that are provided herein for purposes of illustration only and are not intended to limit the scope of the invention.

EXAMPLES

Example 1

Experimental Procedures

Plant Growth

Plants were grown in florescent light under long-day conditions (16 hours light, 8 hours dark). Wild type was Columbia. Transgenic plants were generated by vacuum infiltration (Bechtold et al. (1993) C. R. Acad. Sci. 316:1194–1199). For root gravitropism experiments, seeds were grown on vertically oriented 1/2×MS plates at 24° C.

In situ Hybridization and Histological Analysis

Antisense probes for in situ hybridization were generated from pDW221 (UFO) (Lee et al., 1997); the 5' region of FIL subcloned into pBluescript (Siegfried et al., 1999); pAS66 containing nucleotides 1165–1787 of the CLV1 cDNA cloned into pBluescript (a gift from A. Sessions); and three MP cDNA fragments subcloned into pSP72 (Hardtke and Berleth, 1998). Tissue preparation, hybridization and signal detection were essentially as described (Ferrándiz et al., 1999). Tissue for whole-mount analysis was prepared as described (Berleth and Jürgens, 1993), and viewed under dark-field illumination in a dissecting microscope. GUS assays were as described (Blázquez et al. (1997) Development 124:3835–3844).

Cloning and Identification of PID pid-9 genomic DNA was digested with Hind III (right border rescue) and Bam HI (left border rescue), and plasmids were recovered as described (Weigel et al., 2000). Both PID exons were amplified separately from genomic DNA of pid mutants. The resulting PCR fragments were gel purified and sequenced using an ABI DNA Sequencing Kit (Perkin Elmer, Foster City, Calif.).

cDNA Synthesis and Subcloning

RT-PCR was performed on total mRNA extracted from Arabidopsis inflorescences using the Reverse Transcription System Kit (Promega, Madison, Wis.). The first strand was synthesized using an oligo dT primer. Subsequent PCR amplification was performed using two sets of gene-specific primers that amplified sequences from the initiation codon to 36 bp downstream of the stop codon. These were cloned into the GST-fusion vector pGEX4T-1 for expression in bacteria, and into the binary T-DNA vector CHF3, a derivative of pPZP212 (Hajdukiewicz et al. (1994) Plant Mol. Biol. 25:989–994) containing a CaMV 35S promoter/nos 3' cassette and carrying the kanamycin resistance gene (a gift from C. Fankhauser), for expression in plants. Mutations were introduced into the GST:PID and 35S::PID constructs by PCR using the QuikChange Site-Directed Mutagenesis Kit (Stratagene, La Jolla, Calif.).

Protein Kinase Assays

Bacteria transformed with wild-type and mutant GST:PID constructs were induced with 1 mM IPTG when $OD_{600}$ was 0.5 to 0.7. Culture was continued overnight at 18° C. After collecting the bacterial pellet by centrifugation, it was incubated on ice with extraction buffer (EB) (150 mM NaCl, 2 mM KCl, 2 mM $KH_2PO_4$, 10 mM $Na_2HPO_4$, 2 mM EDTA, 2 mM DTT, 0.02% Pefabloc [Boehringer Mannheim]) for 30 minutes, followed by sonication for 2 minutes. Triton X-100 was added to 1%. The soluble fraction was isolated by spinning 10 min at 14,000 rpm in an Eppendorf centrifuge. 1.0 ml of the soluble fraction was added to 200 µl of a slurry of Glutathione agarose beads (Sigma) pre-equilibrated in EB and 1% Triton X-100, and tubes were rocked for one hour at 4° C. Beads were washed three times with EB and twice with HDE (20 mM HEPES, 5 mM DTT, 5 mM EDTA). For kinase assays, 10 µl of glutathione beads containing the bound protein were mixed with 4 µl 5×kinase buffer (125 mM Tris pH 7.5, 25 mM $MgCl_2$, 1 mM EDTA), 1 µl [$\gamma$-$^{32}$P] ATP (specific concentration 3000 Ci/mM), 0.2 µl 10 mM ATP, and 4.8 µl $dH_2O$, and incubated for 30 minutes at 30° C. After extensive washes with EB, one volume of FSB (250 mM Tris/HCl pH 6.8, 2% SDS, 30% glycerol, 0.1 M DTT, 0.02% bromophenol blue) was added to each sample. Samples were boiled for three minutes, spun briefly and 15 µl of the supernatant was separated on pre-cast 4–15% polyacrylamide gels (BIO-RAD). After staining, gels were dried and exposed overnight to Kodak BIO-MAX film.

TABLE 2

Root growth in response to exogenous auxin in 35S:PID plants.
Primary root length of 35S::PID plants was much more variable than that of wild-type plants.

| [NAA] (µM) | Primary root length (mm)* | Lateral roots* | n |
| --- | --- | --- | --- |
| 0 | 12.2 ± 5.1 | 0.5 ± 0.8 | 14 |
| 0.1 | 11.6 ± 5.9 | 0.1 ± 0.3 | 11 |
| 1 | 6.0 ± 3.1 | 0.1 ± 0.3 | 14 |
| 10 | 1.4 ± 0.5 | 0.7 ± 1.2 | 12 |

*Mean ± standard deviation

Example 2

Cloning of PINOID

The pinoid-9 (pid-9) mutant was isolated in a screen of a T2 population of plants derived from parents transformed with the activation tagging vector pSKI015. Non-complementation testing using a previously identified pid allele was performed to confirm that this mutant represented a new allele at the PINOID locus.

Standard genetic segregation analysis was used to determine that the pid-9 mutation is recessive and that it is closely linked to the T-DNA insertion by virtue of its co-segregation with resistance to the herbicide ammonium glufosinate. These data indicated that the pid-9 allele was a good candidate for insertional cloning. Southern blot analysis indicated that there are at least two copies of the pSKI015 vector inserted in the genome of pid-9 plants. However, the segregation data are consistent with a tandem integration of multiple plasmids at a single site in the genome.

To recover plant DNA flanking the insertion site in pid-9 mutants, DNA was prepared from homozygous mutant plants and digested with multiple restriction enzymes including HindIII, BamIII, EcoRI and KpnI, which allowed the recovery of DNA from both the left and right borders of the insertion. After digestion, the rescuing DNA fragments were ligated under conditions that favor intra-molecular recombination, transformed into bacteria and plated on selective media. Rescued plasmids were obtained for all the enzymes used. The plasmids were sequenced and the resulting sequence for each plasmid was used to search both the GenBank and *Arabidopsis thaliana* databases.

These sequences located a perfect match with BAC clone T31E10, accession number AC004077. All the rescued plasmids identified the same genomic BAC clone; in addition, sequences from the right- and left-border rescued plasmids identified contiguous sequence within this clone. The genomic clone identified by the rescued plasmids was positioned between two markers on the physical map on the South arm of chromosome II. This position correlates very closely with the genetic map position of PINOID as determined previously (Bennet et al, *The Plant Journal,* 8(4), 505–520, 1995).

The T-DNA insertion in the pid-9 mutant disrupted the coding region of a putative protein with extensive homology to several classes of putative serine threonine protein kinases (FIGS. 2A and B). Table 1 below shows a comparison of the mRNA of pid-9 with that of *Brassica rapa* putative serine/threonine protein kinase (Bcpk1) (GeneBank No. U93559).

The insertion point in pid-9 was in the first exon and resulted in a 23 bp deletion adjacent to the site of insertion. To confirm that this predicted gene was expressed in Arabidopsis, plant specific DNA from one of the rescued plasmids was used as a probe to screen 300,000 plaques from each of two cDNA libraries. One partial and one full length clone were recovered from one library, indicating that the open reading frame disrupted in the pid-9 mutant represents a transcribed gene. Comparison of the sequence of the longest clone with the genomic sequence from BAC T31E10 indicated that this clone was unspliced. To obtain a spliced transcript we performed RT-PCR using total Arabidopsis RNA. First strand synthesis was performed using an oligo (dT) primer and subsequent amplification was carried out using gene specific primers derived from the original cDNA isolated.

To confirm that this kinase actually represent the PINOID gene, genomic DNA from eight previously identified PINOID mutant alleles pid-1 through pid-8) was extracted, the presumed PINOID coding region was PCR amplified and the resulting PCR fragments were directly sequenced. For each pid allele, a molecular lesion was found in the kinase gene identified by the pid-9 mutation As shown by FIG. 2, these lesions included two nonsense alleles (pid-1 and pid-6), five missense alleles (pid-2, pid-3, pid-5, pid-6 and pid-8) and one deletion mutant (pid-7). For each mutant, the original DNA was reamplified and the mutation was confirmed by sequencing of the independent PRC product. Subsequently, a tenth allele, pid-10, was provided. After confirming the identity of the mutant pid-10 by non-complementation testing, this allele was sequenced as above and found to encode a sixth missense mutation.

The PINOID cDNA obtained by RT-PCR was cloned into the bacterial expression vector pGEX-4T-1, and the GST fusion protein was expressed in bacteria. After purification on GST beads, the protein was shown to be an active kinase in vitro by assaying for autophosphorylation using known methods. In parallel, a protein expressed from a plasmid containing an introduced mutation in the catalytic domain (MPID) was shown to be inactive under the same conditions (See description of FIG. 3).

This experiment also indicates that the PINOID protein kinase is a functional kinase despite the occurrence of a substitution in one of the 14 amino acid residues heretofore considered to be universally conserved in protein kinases, i.e., a single amino acid substitution (DFG=>DFD) at amino acid 225. The DFD locus has been determined to be implicated in ATP-binding in the catalytic domain in PINOID.

Example 3

Expression of Meristem Markers in pid Inflorescences

The pin-like inflorescence produced by pid loss-of-function mutants suggests that PID is required either to regulate patterning within the shoot apical meristem, or more specifically to direct lateral meristem formation. To distinguish between these possibilities, the expression of several genes that are expressed in the developing inflorescence or in emerging floral primordia of wild-type plants were examined. CLV1 and UFO are expressed in a complementary pattern in the shoot apex: CLV1 is expressed in sub-epidermal layers at the center of the apex in the region corresponding to the meristem proper (Clark et al. (1997) *Cell* 89:575–585), while UFO is expressed in a cup-shaped region surrounding the meristematic core of the apex (Lee et al. (1997) *Curr. Biol.* 7:95–104; Long and Barton (1998) *Development* 125:3027–3035). The expression of both genes in the apical meristem of pid mutant pins was similar to that seen in wild-type plants.

MP and FILAMENTOUS FLOWER (FIL) were used to examine lateral meristem formation in the pid inflorescence. In the wild-type inflorescence, MP is strongly expressed in floral anlagen and emerging flowers and more weakly in the developing vasculature (Hardtke and Berleth, 1998). FIL is expressed in a small abaxial domain in the flower anlagen and emerging floral primordia (Sawa (1999) *Genes Dev.* 13:1079–1088; Siegfried et al. (1999) *Development* 126:4117–4128). MP was strongly expressed in pid apices along with weaker expression in the developing vasculature. While FIL RNA was detected in pid mutants, FIL was only weakly expressed in discrete foci on the flanks of the inflorescence apex, indicating that early development of lateral primordia was defective in pid mutants.

Because PID and PIN share a similar loss-of-function phenotype, the expression of PIN in pid mutants was also investigated. In wild-type plants, PIN is expressed in both the vasculature (Gälweiler et al., 1998) and in developing flowers (FIG. 1I), similar to the MP expression domains. In the pid inflorescence, PIN was expressed in a small group of cells on the flanks of the shoot apical meristem and in the procambium, in a pattern similar to that observed in wild-type plants.

Example 4

Petal and Carpel Venation in pid Mutants

Auxin signaling controls vascular patterning in the cotyledons, leaves, stems and flowers of Arabidopsis (Sessions and Zambryski (1995) *Development* 121:1519–1532; Przemeck et al., 1996; Gälweiler et al., 1998; Mattsson et al. (1999) *Development* 126:2979–2991). Because of the similar inflorescence phenotype of pid mutants with those of plants mutant for the auxin transporter PIN and the ARF MP, which are required for vascular patterning (Gälweiler et al., 1998; Mattsson et al., 1999), this aspect of auxin response was disrupted in pid mutants as well. While the venation of non-floral tissues including cotyledons, rosette leaves and inflorescence stems was normal in pid mutants, vascular elements within the pid flower were abnormally formed.

Two female reproductive organs, the carpels, form the central gynoecium of the Arabidopsis flower (Smyth et al. (1990) Plant Cell 2:755–767). Its primary vascular system is composed of four vascular bundles that run parallel to its longitudinal axis (Sessions and Zambryski, 1995). One lateral bundle runs the length of each valve, which makes up the outer wall of the ovary, and terminates just below the junction between valve and style. The two opposing medial bundles arise in the margins of the septum, which bisects the gynoecium and forms the inner wall of the ovary. Within the ovary, lateral branches of the medial bundles supply the individual ovules. After entering the style, immediately distal to the valves, each medial bundle branches to form a fan of xylem on the medial face of the style.

The weak allele pid-8 had variable defects characterized by reduced valve formation and distal displacement of valve tissues. pid-8 gynoecia frequently developed only a single carpel, and the lateral vascular bundle that normally supplies the missing valve was deleted. In the reduced valve tissues, primary and secondary lateral vascular elements differentiated normally. Despite the relatively normal morphology of these valves, pid-8 gynoecia frequently lacked ovular xylem. Regardless of valve number, two medial xylem bundles were consistently observed. However, these bundles branched prematurely, proximal to the valve/style junction, and the vascular fans formed on the lateral, rather than the medial face of the style.

In the few flowers that formed in strong pid-9 mutants, valves were usually replaced by tissue that resembled the wild-type style. Consistent with this replacement, lateral vascular bundles were missing. Valves and lateral bundles are absent. As in the weak pid-8 allele, medial bundles differentiated normally, but branched prematurely. In pid-9, the medial bundles began to branch close to the mid-point of the reduced gynoecium. This premature branching resulted in the formation of supernumerary xylem fans that encircled the distal tip of the gynoecium. In addition to defects in the carpel, pid-9 petals occasionally showed defects in vascular continuity as well, and the vascular loops characteristic of wild-type petals were often replaced by linear veins that terminated near the petal margin.

Example 5

PID Encodes a Serine-Threonine Protein Kinase

The recessive pid-9 mutant was isolated from a T2 population of plants transformed with the activation-tagging vector pSKI015. Segregation analysis revealed that the pid-9 mutation was closely linked to the T-DNA insertion. Plant DNA flanking the left and right borders of the insertion was recovered by plasmid rescue and sequenced. The T-DNA in pid-9 was found to be inserted in the genomic sequence represented in BAC T31E10, whose position on the physical map correlated closely with the genetic map position of PID on chromosome II (Bennett et al., 1995).

The T-DNA insertion in pid-9 disrupted the coding region of an annotated gene (Accession AAC26704) with a single intron. No cDNA in 600,000 clones of a floral cDNA library were found (Weigel et al. (1992) Cell 69:843–859), indicating that transcripts of this gene are rare. The gene structure predicted from the genomic sequence was confirmed by reverse transcription followed by polymerase chain reaction. To establish that this gene represented the PID locus, the coding region of this gene was sequenced in twelve pid mutant alleles. For each allele, a mutation was found in the gene disrupted by the pid-9 T-DNA. These lesions included two nonsense mutations, ten missense mutations, and one small deletion (Table 1; FIG. 3A).

TABLE 1

Sequence changes in pid alleles.

| Allele | Effect | Strain[a] | Origin | Codon change | Amino acid change |
|---|---|---|---|---|---|
| 1 | strong | Ler | Bennett et al., 1995 | CGA→TGA | R53stop |
| 2 | intermed. | Ler | Bennett et al., 1995 | GGG→AGG | G380R |
| 3 | strong | Col | Bennett et al., 1995 | CTC→TTC | L226F |
| 4 | strong | Ler | Bennett et al., 1995 | AGA→AAA | R378K |
| 5 | strong | Ler | Bennett et al., 1995 | GAG→AAG | E128K |
| 6 | strong | Ler | Bennett et al., 1995 | CGA→TGA | R63stop |
| 7 | strong | Ler | Bennett et al., 1995 | 38 bp Δ (964 to 1001) | truncation after L321 |
| 8 | weak | Ws-2 | Bennett et al., 1995 | CCA→CAA | P300Q |
| 9 | strong | Col | This study | 23 bp Δ (526–548); T-DNA insertion | truncation after R175 |
| 10 | intermed. | No-O | Jennifer Fletcher | GGC→AGC | G84S |
| 11 | strong | Col | Ray Hong | GAG→AAG | E128K |
| 12 | strong | Col | Allen Sessions | AGA→AAA | R378K |
| 13 | weak | Ws-2 | Allen Sessions | CAC→TAC | H166Y |

[a]Ler, Landsberg erecta; Col, Columbia; Ws-2, Wassilewskija-2; No-O, Nossen.

The predicted PID protein of 438 amino acids shares extensive similarity with several classes of serine-threonine protein kinases (FIG. 3A). The homology of PID to the catalytic domain of protein kinases extends the length of the predicted protein and contains all eleven subdomains typical of protein kinases (Hanks et al. (1988) Science 241:42–52). Comparison of PID with the consensus sequence derived from yeast and animal protein kinases revealed that PID contained 13 of the 14 invariant amino acids that define the catalytic domain. The single exception was the replacement of an invariant glycine at position 225 with aspartate, changing the conserved DFG motif to DFD. A stretch of approximately 50 amino acids between the conserved subdomains VII and VIII may represent a regulatory domain.

All but one of the missense mutations were either in, or within two amino acids from, one of the kinase-typical invariant residues.

To determine whether PID is a functional protein kinase, the protein was expressed as a GST fusion product in *E. coli*. To examine the importance of specific residues within the kinase domain, and of the potential regulatory region between domains VII and VIII, several PID derivatives were generated by site-directed mutagenesis.

As a negative control, ASp$^{205}$ was replaced with Ala, inactivating the ATP binding domain (GST:MPID). The importance of the DFD as opposed to the canonical DFG motif was addressed with a change of Asp$^{225}$ to Gly in GST:DFG. Finally, two fusion constructs were made to test the function of serines and threonines adjacent to the potential regulatory domain, by introducing negatively charged glutamate residues, which mimic phosphoserine or phosphothreonine. GST:ALT contained a Thr$^{294}$ to Glu substitution, and GST:ALS contained Glu substitutions at both Ser$^{288}$ and Ser$^{290}$.

The wild-type fusion, GST:PID, auto-phosphorylated in vitro, while the GST:MPID fusion protein was inactive. Bacterially produced GST-PID fusion protein and derivatives were incubated with $^{32}$p labeled ATP and separated by PAGE. Both GST:ALS and GST:DFG autophosphorylated, with an apparent increase in activity in GST:DFG relative to wild-type GST:PID. GST:ALT did not show any autophosphorylation, indicating that it was either inactive, or that Thr294 is the major autophosphorylation site.

Example 6

Expression Pattern of PID pid loss-of function mutants exhibit morphological defects at both early and late stages of development. In wild-type plants, two opposing cotyledons are formed during embryogenesis. The arrangement of the first pair of true leaves, which normally form perpendicularly to the cotyledons, is dependent on the position of the cotyledons. pid mutant embryos often develop three symmetrically arranged cotyledons, followed by three primary leaves that arise between the cotyledons. The rest of the vegetative shoot system develops normally in pid mutants. Defects become apparent again after the switch to the reproductive phase, when PID is required for floral meristem outgrowth and floral organ development (Bennett et al., 1995).

To determine whether these stage-specific phenotypes correlated with the temporal expression pattern of PID transcripts, and to determine where in the embryo and shoot PID acts to control morphogenesis, PID RNA accumulation by in situ hybridization was examined. The earliest point at which PID expression was detectable was during the globular stage of embryogenesis. PID was initially expressed on the apical flanks of the globular stage embryo, where the cotyledons will subsequently form (Jürgens and Mayer (1993) Arabidopsis. In A Colour Atlas of Developing Embryos, J. Bard, ed. (London: Wolfe Publ.), pp. 7–21). Expression in the cotyledons persisted throughout the heart until the mid-torpedo stage. During the heart stage, expression becomes confined to the outer layers of the incipient cotyledons (cot), as well as the flanks of the presumptive hypocotyl (hy). It is absent from the embryonic root, the radicle (ra). By the bent-cotyledon stage, PID expression was only weakly detected in the shoot apical meristem.

Similarly, PID was only weakly expressed in the shoot apex and in young leaves of vegetatively growing plants. During the vegetative phase, PID is expressed weakly on the flanks of the shoot apical meristem (sam). The levels of PID RNA increased after the transition to reproductive development, although overall levels were low in comparison to those of other auxin-related genes such as PIN or MP. In the inflorescence, PID was expressed in discrete groups of cells on the flanks of the apex, which initially marked the floral anlagen. In the inflorescence, PID is expressed more strongly at the flanks of the shoot apical meristem, but has been excluded from most of a stage 1 flower, except for a small adaxial patch. Expression reappears on the flanks of a stage 2 flower. In the stage 5 flower, expression is apparent in the central floral meristem, but not in the outer whorl of sepals (se). As soon as floral primordia became morphologically distinct, PID RNA became restricted to the adaxial portion of the primordia. The initial expression pattern of PID in stage 3 flowers, which were about to form sepals, mimicked that of the expression pattern in the shoot apex. In developing flowers, PID was transiently expressed in nascent floral organs. In a stage 7 flower, PID expression is apparent along the outer layers of the stamen (st) primordia, with lower levels in the central gynoecium (g). As floral organs matured, PID transcripts were down regulated.

Because pin and pid mutants have similar inflorescence phenotypes, the expression of PID in pin-1 mutants was examined. PID was weakly expressed at the flanks of the apex in pin-1 mutants, indicating that changes in auxin levels in pin-1 mutants did not affect PID expression.

Example 7

Consequences of Ectopic PID Expression

To determine whether PID is limiting for auxin signaling, the PID cDNA was expressed under the control of the CaMV 35S promoter, which is constitutively active in most plant tissues (Odell et al. (1985) Nature 313:810–812). Nine of 170 primary 35S::PID transformants had a phenotype different from that of wild-type plants. Loss of apical dominance results in the simultaneous formation of multiple inflorescence shoots. Northern analysis of total RNA prepared from transgenic plants with this new phenotype and from transgenic plants that were phenotypically normal confirmed that PID was overexpressed only in the former. Hemizygous 35S::PID plants were small and had dark green, curled leaves. Eight of the nine T1 plants with vegetative defects also showed defects during the reproductive phase, with reduced apical dominance and reduced internode elongation. Four of these T1 plants were sterile, while the other four 35S::PID T1 plants were semi-fertile. As a control, plants with the 35S::MPID construct were transformed which lacked in vitro kinase activity. Of 69 T1 plants, none showed the 35S::PID phenotype, confirming that PID functions as a protein kinase in vivo. Despite the severe morphological defects in the shoot system of 35S::PID plants, which were reminiscent of those seen in auxin-insensitive and auxin-resistant plants (Lincoln et al. (1990) Plant Cell 2:1071–1080), the vasculature of rosette leaves was largely normal, indicating that PID overexpression did not equally affect all auxin-regulated processes.

One 35S::PID line was chosen for further characterization. In the T2 progeny of this line a more severe phenotypic class was observed, consisting of extreme dwarves. These plants constituted approximately 10% of the T2 progeny and were sterile. Of the fertile T2 plants, two thirds (139/207) carried the kanamycin-resistance marker of the transgene and showed the same phenotype as the T1 parent, while the remaining third (68/207) was phenotypically wild type and sensitive to kanamycin. Segregation analysis of T3 progeny of twelve fertile T2 plants confirmed that each T2 plant had been hemizygous for the transgene, suggesting that the extreme dwarves had been homozygous. Since homozygous progeny were apparently under-represented, it was likely that the majority of homozygous plants died as embryos, or failed to germinate.

It was determined whether ectopic expression of PID could affect auxin-regulated processes in the root as well. Two such processes have been particularly well studied using Arabidopsis mutants, namely gravitropism and lateral root initiation (Maher and Martindale (1980) Biochem. Genet. 18:1041–1053; Lincoln et al., 1990; Bennett et al., 1996; Leyser et al. (1996) Plant J. 10:403–413; Ruegger et al., 1997; Chen et al., 1998; Luschnig et al., 1998; Müller et al., 1998; Tian and Reed, 1999), and PID overexpression affected both of them. 35S::PID plants had either no or very few lateral roots, and roots grew aberrantly across the surface of the substrate instead of into it. The aberrant root growth was due to lack of a gravitropic response, as determined by growing segregating T2 progeny without selection on vertical plates. After 18 days, 15 of 24 T2 germinated seedlings had no lateral roots, and two seedlings had one lateral root. The remaining seven plants generated an average of ten lateral roots (range 4–16). Primary root growth in seedlings lacking lateral roots was random with respect to the gravity vector, while seedlings with more than one lateral root responded normally, indicating that the lateral root defect and the gravitropic defect were genetically linked. Progeny of a hemizygous 35S::PID plant segregated normal seedlings with numerous lateral roots and normal gravitropism and abnormal seedlings that lacked lateral roots and had short agravitropic roots.

To determine whether the loss of lateral root formation in 35::PID plants could be bypassed by exogenous auxin, T2 plants were grown on plates supplemented with the synthetic auxin-analog NAA (β-napthaleneacetic acid). After 10 days on 0.1 μm NAA, 11 of 37 germinated seedlings had produced an average of 24 lateral roots (range, 18–31), while the remaining 26 had failed to produce lateral roots, indicating that NAA did not overcome the block in lateral root formation caused by PID overexpression. As in the previous experiment, there was a perfect correlation between loss of lateral root formation and agravitropic root growth.

The failure of 35S::PID plants to develop lateral roots in response to exogenous auxin can be explained by defects in either auxin uptake or response. To distinguish between these possibilities, 35S: PID plants was selected on plates containing kanamycin and 0, 0.1, 1.0 or 10.0 μM NAA. Although in the absence of auxin 35S::PID plants already had shorter primary roots than wild type, primary root elongation in 35S::PID plants was progressively inhibited with increasing NAA concentration, indicating that auxin uptake into the root was not blocked. However, even at very high NAA concentrations, lateral root growth was still inhibited, indicating that 35S::PID plants were specifically deficient in lateral root formation.

Finally, to assay the effect of PID overexpression more directly, 35S::PID was crossed to plants carrying the DR5::GUS reporter, which contains a multimerized synthetic auxin response element that is bound by ARF transcription factors (Ulmasov et al., 1997b). GUS activity in the root tips of 35S::PID plants was reduced compared to plants that did not overexpress PID, indicating that PID could negatively regulate this particular auxin response as well.

The phenotype of 35S::PID plants supports the idea that PID negatively regulates auxin signaling. In the aerial part of the plant, PID overexpression results in dwarf stature, decreased apical dominance and leaf curling. In the root, overexpression of PID leads to agravitropic growth and the absence of lateral roots. In contrast to PID overexpressers, pid mutants do not have an obvious root phenotype and respond normally to exogenous auxin, suggesting that in wild-type plants different PID homologs regulate tissue-specific auxin responses similar to the tissue-specific roles proposed for the PIN/EIR1/AGR1 family of auxin transporters.

While the invention has been described in detail with reference to certain preferred embodiments thereof, it will be understood that modifications and variations are within the spirit and scope of that which is described and claimed.

What is claimed is:

1. A purified polynucleotide, wherein the polynucleotide comprises a nucleic acid encoding a polypeptide having the amino acid sequence of SEQ ID NO: 2.

2. A purified polynucleotide, wherein the polynucleotide comprises a nucleic acid encoding a plant kinase capable of auto-phosphorylation and comprising an aspartic acid-phenylalanine-aspartic acid (DFD) motif in catalytic subdomain VII, and wherein said nucleic acid comprises a nucleic acid sequence with at least 95% sequence identity to SEQ ID NO: 1.

3. The purified polynucleotide acid of claim 1, wherein the nucleic acid has the sequence of SEQ. ID. NO: 1.

4. An expression vector comprising the polynucleotide according to claim 2.

5. The expression vector of claim 4, wherein the vector is a plasmid.

6. The expression vector of claim 5, wherein the plasmid is the Ti plasmid of *Agrobacterium tumefaciens*.

7. The expression vector of claim 5, wherein the plasmid is the Ri plasmid of *Agrobacterium tumefaciens*.

8. A host cell containing the expression vector of claim 4.

9. An expression vector comprising the polynucleotide according to claim 1.

10. The expression vector of claim 9, wherein the vector is a plasmid.

11. The expression vector of claim 10, wherein the plasmid is the Ti plasmid of *Agrobacterium tumefaciens*.

12. The expression vector of claim 10, wherein the plasmid is the Ri plasmid of *Agrobacterium tumefaciens*.

13. A host cell containing the expression vector of claim 9.

* * * * *

SEQUENCE LISTING

```
<160> NUMBER OF SEQ ID NOS: 6

<210> SEQ ID NO 1
<211> LENGTH: 1643
<212> TYPE: DNA
<213> ORGANISM: Arabidopsis thaliana
<220> FEATURE:
<221> NAME/KEY: CDS
<222> LOCATION: (214)...(1531)

<400> SEQUENCE: 1
ccttcttcca tctctctcaa acttctgaaa atcttcttct tcttctcaat cataaaccct      60
aaatcttcat ctcttcagat cagaaactaa tgtccattca aagacaccct gtcctgtttc     120
atctctgtca ttagtcttct gttttcagat tccaattttt ttcttgaatt atcctcttag     180
ccatttcttg atttaacttc gatttteccg gcg atg tta cga gaa tca gac ggt     234
                                  Met Leu Arg Glu Ser Asp Gly
                                   1               5 gag atg agt tta gga aca aca aac tca ccg ata agc agc gga aca gag     282
```

```
Glu Met Ser Leu Gly Thr Thr Asn Ser Pro Ile Ser Ser Gly Thr Glu
         10                  15                  20 agt tgc agc agt ttc agc cgg tta tca ttc gac gcg ccg ccg tca act        330
Ser Cys Ser Ser Phe Ser Arg Leu Ser Phe Asp Ala Pro Pro Ser Thr
     25                  30                  35 atc ccc gaa gaa gaa agc ttc ctt tct ctc aaa cct cac cga tcc tca        378
Ile Pro Glu Glu Glu Ser Phe Leu Ser Leu Lys Pro His Arg Ser Ser
 40                  45                  50                  55 gat ttc gct tac gca gag atc cga aga cga aaa aaa caa ggc cta acc        426
Asp Phe Ala Tyr Ala Glu Ile Arg Arg Arg Lys Lys Gln Gly Leu Thr
                 60                  65                  70 ttc cga gat ttt cgc ctc atg cgt cgt atc ggc gcc ggc gac atc gga        474
Phe Arg Asp Phe Arg Leu Met Arg Arg Ile Gly Ala Gly Asp Ile Gly
             75                  80                  85 aca gtt tac tta tgc cgt cta gcc gga gac gaa gaa gag agc cgg agc        522
Thr Val Tyr Leu Cys Arg Leu Ala Gly Asp Glu Glu Glu Ser Arg Ser
         90                  95                 100 tcg tat ttt gcg atg aaa gtt gtg gat aaa gaa gct ctt gcg ttg aag        570
Ser Tyr Phe Ala Met Lys Val Val Asp Lys Glu Ala Leu Ala Leu Lys
     105                 110                 115 aag aag atg cat aga gca gag atg gag aaa acg att ttg aaa atg ctt        618
Lys Lys Met His Arg Ala Glu Met Glu Lys Thr Ile Leu Lys Met Leu
120                 125                 130                 135 gac cat cca ttt ttg ccg act ctt tac gct gag ttt gaa gcc tca cat        666
Asp His Pro Phe Leu Pro Thr Leu Tyr Ala Glu Phe Glu Ala Ser His
                 140                 145                 150 ttc tct tgc atc gtt atg gaa tat tgc tcc ggt ggt gat tta cac tct        714
Phe Ser Cys Ile Val Met Glu Tyr Cys Ser Gly Gly Asp Leu His Ser
             155                 160                 165 ctc cgt cat aga caa cct cac cgg cga ttc tcc ctc tct tcc gcc aga        762
Leu Arg His Arg Gln Pro His Arg Arg Phe Ser Leu Ser Ser Ala Arg
         170                 175                 180 ttt tat gcc gcc gaa gtt cta gtg gcg tta gaa tat cta cac atg ttg        810
Phe Tyr Ala Ala Glu Val Leu Val Ala Leu Glu Tyr Leu His Met Leu
     185                 190                 195 ggt atc atc tac aga gat ctg aag cct gaa aat atc tta gtt aga tcc        858
Gly Ile Ile Tyr Arg Asp Leu Lys Pro Glu Asn Ile Leu Val Arg Ser
200                 205                 210                 215 gac ggt cac att atg ctc tct gac ttt gac ctc tct cta tgc tcc gac        906
Asp Gly His Ile Met Leu Ser Asp Phe Asp Leu Ser Leu Cys Ser Asp
                 220                 225                 230 tca atc gca gcc gtt gaa tct tcc tcg tct tcg ccg gag aat caa caa        954
Ser Ile Ala Ala Val Glu Ser Ser Ser Ser Ser Pro Glu Asn Gln Gln
             235                 240                 245 ctc cgt tca ccg cga cga ttc act cgt ctc gct aga ctt ttc caa cga       1002
Leu Arg Ser Pro Arg Arg Phe Thr Arg Leu Ala Arg Leu Phe Gln Arg
         250                 255                 260 gtc ttg cgg tct aaa aag gtt cag act tta gaa cca acc cgt ctc ttt       1050
Val Leu Arg Ser Lys Lys Val Gln Thr Leu Glu Pro Thr Arg Leu Phe
     265                 270                 275 gtt gct gaa ccg gtt act gcc cgg tcc ggt tcg ttc gtt ggt acg cat       1098
Val Ala Glu Pro Val Thr Ala Arg Ser Gly Ser Phe Val Gly Thr His
280                 285                 290                 295 gaa tac gtg gca cca gaa gtt gct tca ggt gga tca cat ggt aat gcc       1146
Glu Tyr Val Ala Pro Glu Val Ala Ser Gly Gly Ser His Gly Asn Ala
                 300                 305                 310 gtt gac tgg tgg gcc ttt gga gtg ttt ctc tac gag atg ata tat ggc       1194
Val Asp Trp Trp Ala Phe Gly Val Phe Leu Tyr Glu Met Ile Tyr Gly
             315                 320                 325
```

-continued

| | | |
|---|---|---|
| aag act ccg ttc gtt gcg ccg act aat gac gtc att ctc cgt aac att<br>Lys Thr Pro Phe Val Ala Pro Thr Asn Asp Val Ile Leu Arg Asn Ile<br>330               335               340 | | 1242 |
| gtg aaa aga cag ttg agt ttc ccg act gat tcg ccg gcg act atg ttt<br>Val Lys Arg Gln Leu Ser Phe Pro Thr Asp Ser Pro Ala Thr Met Phe<br>345               350               355 | | 1290 |
| gag ctt cat gcg cgg aat ttg att tcc ggg ttg ctt aac aaa gat ccg<br>Glu Leu His Ala Arg Asn Leu Ile Ser Gly Leu Leu Asn Lys Asp Pro<br>360               365               370               375 | | 1338 |
| act aaa aga ctt ggg tca cgg cga ggt gcg gcg gag gtt aaa gtg cat<br>Thr Lys Arg Leu Gly Ser Arg Arg Gly Ala Ala Glu Val Lys Val His<br>              380               385               390 | | 1386 |
| cct ttt ttc aaa ggt cta aac ttt gcg ctc att cgt acg ctt act ccg<br>Pro Phe Phe Lys Gly Leu Asn Phe Ala Leu Ile Arg Thr Leu Thr Pro<br>395               400               405 | | 1434 |
| ccg gag att cct tct tcc gtc gtc aag aag ccg atg aaa tcg gcg acg<br>Pro Glu Ile Pro Ser Ser Val Val Lys Lys Pro Met Lys Ser Ala Thr<br>              410               415               420 | | 1482 |
| ttt agt ggt aga agt agt aac aaa cca gcg gcg ttc gat tac ttt tga<br>Phe Ser Gly Arg Ser Ser Asn Lys Pro Ala Ala Phe Asp Tyr Phe *<br>425               430               435 | | 1530 |
| a cgttttctac ggtcgagatt agggccacgt gttagtctgt tttagctgta | | 1581 |
| catattccct cgaagctgtc cttttttcg ttctttaatt tttaaaattt cgttaatctg | | 1641 |
| ac | | 1643 |

<210> SEQ ID NO 2
<211> LENGTH: 438
<212> TYPE: PRT
<213> ORGANISM: Arabidopsis thaliana

<400> SEQUENCE: 2

Met Leu Arg Glu Ser Asp Gly Glu Met Ser Leu Gly Thr Thr Asn Ser
1               5                   10                  15

Pro Ile Ser Ser Gly Thr Glu Ser Cys Ser Ser Phe Ser Arg Leu Ser
            20                  25                  30

Phe Asp Ala Pro Pro Ser Thr Ile Pro Glu Glu Glu Ser Phe Leu Ser
        35                  40                  45

Leu Lys Pro His Arg Ser Ser Asp Phe Ala Tyr Ala Glu Ile Arg Arg
    50                  55                  60

Arg Lys Lys Gln Gly Leu Thr Phe Arg Asp Phe Arg Leu Met Arg Arg
65                  70                  75                  80

Ile Gly Ala Gly Asp Ile Gly Thr Val Tyr Leu Cys Arg Leu Ala Gly
                85                  90                  95

Asp Glu Glu Glu Ser Arg Ser Tyr Phe Ala Met Lys Val Val Asp
            100                 105                 110

Lys Glu Ala Leu Ala Leu Lys Lys Met His Arg Ala Glu Met Glu
        115                 120                 125

Lys Thr Ile Leu Lys Met Leu Asp His Pro Phe Leu Pro Thr Leu Tyr
    130                 135                 140

Ala Glu Phe Glu Ala Ser His Phe Ser Cys Ile Val Met Glu Tyr Cys
145                 150                 155                 160

Ser Gly Gly Asp Leu His Ser Leu Arg His Arg Gln Pro His Arg Arg
                165                 170                 175

Phe Ser Leu Ser Ser Ala Arg Phe Tyr Ala Ala Glu Val Leu Val Ala
            180                 185                 190

Leu Glu Tyr Leu His Met Leu Gly Ile Ile Tyr Arg Asp Leu Lys Pro

```
            195                 200                 205

Glu Asn Ile Leu Val Arg Ser Asp Gly His Ile Met Leu Ser Asp Phe
    210                 215                 220

Asp Leu Ser Leu Cys Ser Asp Ser Ile Ala Ala Val Glu Ser Ser Ser
225                 230                 235                 240

Ser Ser Pro Glu Asn Gln Gln Leu Arg Ser Pro Arg Arg Phe Thr Arg
                245                 250                 255

Leu Ala Arg Leu Phe Gln Arg Val Leu Arg Ser Lys Lys Val Gln Thr
            260                 265                 270

Leu Glu Pro Thr Arg Leu Phe Val Ala Glu Pro Val Thr Ala Arg Ser
        275                 280                 285

Gly Ser Phe Val Gly Thr His Glu Tyr Val Ala Pro Glu Val Ala Ser
290                 295                 300

Gly Gly Ser His Gly Asn Ala Val Asp Trp Trp Ala Phe Gly Val Phe
305                 310                 315                 320

Leu Tyr Glu Met Ile Tyr Gly Lys Thr Pro Phe Val Ala Pro Thr Asn
                325                 330                 335

Asp Val Ile Leu Arg Asn Ile Val Lys Arg Gln Leu Ser Phe Pro Thr
            340                 345                 350

Asp Ser Pro Ala Thr Met Phe Glu Leu His Ala Arg Asn Leu Ile Ser
        355                 360                 365

Gly Leu Leu Asn Lys Asp Pro Thr Lys Arg Leu Gly Ser Arg Arg Gly
370                 375                 380

Ala Ala Glu Val Lys Val His Pro Phe Phe Lys Gly Leu Asn Phe Ala
385                 390                 395                 400

Leu Ile Arg Thr Leu Thr Pro Pro Glu Ile Pro Ser Ser Val Val Lys
                405                 410                 415

Lys Pro Met Lys Ser Ala Thr Phe Ser Gly Arg Ser Ser Asn Lys Pro
            420                 425                 430

Ala Ala Phe Asp Tyr Phe
            435

<210> SEQ ID NO 3
<211> LENGTH: 38
<212> TYPE: DNA
<213> ORGANISM: Artificial Sequence
<220> FEATURE:
<223> OTHER INFORMATION: pid1-7 mutation

<400> SEQUENCE: 3
tacgagatga tatatggcaa gactccgttc gttgcgcc                            38

<210> SEQ ID NO 4
<211> LENGTH: 23
<212> TYPE: DNA
<213> ORGANISM: Artificial Sequence
<220> FEATURE:
<223> OTHER INFORMATION: pid1-9 mutation

<400> SEQUENCE: 4
cgattctccc tctcttccgc cag                                            23

<210> SEQ ID NO 5
<211> LENGTH: 1643
<212> TYPE: DNA
<213> ORGANISM: Artificial Sequence
<220> FEATURE:
<223> OTHER INFORMATION: PID protein
<221> NAME/KEY: CDS
```

<222> LOCATION: (214)...(1530)

<400> SEQUENCE: 5

```
ccttcttcca tctctctcaa acttctgaaa atcttcttct tcttctcaat cataaaccct      60
aaatcttcat ctcttcagat cagaaactaa tgtccattca aagacaccct gtcctgtttc     120
atctctgtca ttagtcttct gttttcagat tccaattttt ttcttgaatt atcctcttag     180
ccatttcttg atttaacttc gatttcccg gcg atg tta cga gaa tca gac ggt      234
                                    Met Leu Arg Glu Ser Asp Gly
                                     1               5 gag atg agt tta gga aca aca aac tca ccg ata agc agc gga aca gag      282
Glu Met Ser Leu Gly Thr Thr Asn Ser Pro Ile Ser Ser Gly Thr Glu
         10                  15                  20 agt tgc agc agt ttc agc cgg tta tca ttc gac gcg ccg ccg tca act      330
Ser Cys Ser Ser Phe Ser Arg Leu Ser Phe Asp Ala Pro Pro Ser Thr
     25                  30                  35 atc ccc gaa gaa gaa agc ttc ctt tct ctc aaa cct cac cga tcc tca      378
Ile Pro Glu Glu Glu Ser Phe Leu Ser Leu Lys Pro His Arg Ser Ser
 40                  45                  50                  55 gat ttc gct tac gca gag atc cga aga cga aaa aaa caa ggc cta acc      426
Asp Phe Ala Tyr Ala Glu Ile Arg Arg Arg Lys Lys Gln Gly Leu Thr
                 60                  65                  70 ttc cga gat ttt cgc ctc atg cgt cgt atc ggc gcc ggc gac atc gga      474
Phe Arg Asp Phe Arg Leu Met Arg Arg Ile Gly Ala Gly Asp Ile Gly
             75                  80                  85 aca gtt tac tta tgc cgt cta gcc gga gac gaa gaa gag agc cgg agc      522
Thr Val Tyr Leu Cys Arg Leu Ala Gly Asp Glu Glu Glu Ser Arg Ser
         90                  95                 100 tcg tat ttt gcg atg aaa gtt gtg gat aaa gaa gct ctt gcg ttg aag      570
Ser Tyr Phe Ala Met Lys Val Val Asp Lys Glu Ala Leu Ala Leu Lys
    105                 110                 115 aag aag atg cat aga gca gag atg gag aaa acg att ttg aaa atg ctt      618
Lys Lys Met His Arg Ala Glu Met Glu Lys Thr Ile Leu Lys Met Leu
120                 125                 130                 135 gac cat cca ttt ttg ccg act ctt tac gct gag ttt gaa gcc tca cat      666
Asp His Pro Phe Leu Pro Thr Leu Tyr Ala Glu Phe Glu Ala Ser His
                140                 145                 150 ttc tct tgc atc gtt atg gaa tat tgc tcc ggt ggt gat tta cac tct      714
Phe Ser Cys Ile Val Met Glu Tyr Cys Ser Gly Gly Asp Leu His Ser
            155                 160                 165 ctc cgt cat aga caa cct cac cgg cga ttc tcc ctc tct tcc gcc aga      762
Leu Arg His Arg Gln Pro His Arg Arg Phe Ser Leu Ser Ser Ala Arg
        170                 175                 180 ttt tat gcc gcc gaa gtt cta gtg gcg tta gaa tat cta cac atg ttg      810
Phe Tyr Ala Ala Glu Val Leu Val Ala Leu Glu Tyr Leu His Met Leu
    185                 190                 195 ggt atc atc tac aga gat ctg aag cct gaa aat atc tta gtt aga tcc      858
Gly Ile Ile Tyr Arg Asp Leu Lys Pro Glu Asn Ile Leu Val Arg Ser
200                 205                 210                 215 gac ggt cac att atg ctc tct gac ttt gac ctc tct cta tgc tcc gac      906
Asp Gly His Ile Met Leu Ser Asp Phe Asp Leu Ser Leu Cys Ser Asp
                220                 225                 230 tca atc gca gcc gtt gaa tct tcc tcg tct tcg ccg gag aat caa caa      954
Ser Ile Ala Ala Val Glu Ser Ser Ser Ser Ser Pro Glu Asn Gln Gln
            235                 240                 245 ctc cgt tca ccg cga cga ttc act cgt ctc gct aga ctt ttc caa cga     1002
Leu Arg Ser Pro Arg Arg Phe Thr Arg Leu Ala Arg Leu Phe Gln Arg
        250                 255                 260 gtc ttg cgg tct aaa aag gtt cag act tta gaa cca acc cgt ctc ttt     1050
```

```
Val Leu Arg Ser Lys Lys Val Gln Thr Leu Glu Pro Thr Arg Leu Phe
        265                 270                 275 gtt gct gaa ccg gtt act gcc cgg tcc ggt tcg ttc gtt ggt acg cat      1098
Val Ala Glu Pro Val Thr Ala Arg Ser Gly Ser Phe Val Gly Thr His
280                 285                 290                 295 gaa tac gtg gca cca gaa gtt gct tca ggt gga tca cat ggt aat gcc      1146
Glu Tyr Val Ala Pro Glu Val Ala Ser Gly Gly Ser His Gly Asn Ala
            300                 305                 310 gtt gac tgg tgg gcc ttt gga gtg ttt ctc tac gag atg ata tat ggc      1194
Val Asp Trp Trp Ala Phe Gly Val Phe Leu Tyr Glu Met Ile Tyr Gly
                315                 320                 325 aag act ccg ttc gtt gcg ccg act aat gac gtc att ctc cgt aac att      1242
Lys Thr Pro Phe Val Ala Pro Thr Asn Asp Val Ile Leu Arg Asn Ile
        330                 335                 340 gtg aaa aga cag ttg agt ttc ccg act gat tcg ccg gcg act atg ttt      1290
Val Lys Arg Gln Leu Ser Phe Pro Thr Asp Ser Pro Ala Thr Met Phe
345                 350                 355 gag ctt cat gcg cgg aat ttg att tcc ggg ttg ctt aac aaa gat ccg      1338
Glu Leu His Ala Arg Asn Leu Ile Ser Gly Leu Leu Asn Lys Asp Pro
360                 365                 370                 375 act aaa aga ctt ggg tca cgg cga ggt gcg gcg gag gtt aaa gtg cat      1386
Thr Lys Arg Leu Gly Ser Arg Arg Gly Ala Ala Glu Val Lys Val His
            380                 385                 390 cct ttt ttc aaa ggt cta aac ttt gcg ctc att cgt acg ctt act ccg      1434
Pro Phe Phe Lys Gly Leu Asn Phe Ala Leu Ile Arg Thr Leu Thr Pro
                395                 400                 405 ccg gag att cct tct tcc gtc gtc aag aag ccg atg aaa tcg gcg acg      1482
Pro Glu Ile Pro Ser Ser Val Val Lys Lys Pro Met Lys Ser Ala Thr
        410                 415                 420 ttt agt ggt aga agt agt aac aaa cca gcg gcg ttc gat tac ttt tga      1530
Phe Ser Gly Arg Ser Ser Asn Lys Pro Ala Ala Phe Asp Tyr Phe  *
425                 430                 435 acgttttcta cggtcgagat tagggccacg tgttagtctg ttttagctgt acatattccc    1590
tcgaagctgt cctttttttc gttctttaat ttttaaaatt tcgttaatct gac           1643

<210> SEQ ID NO 6
<211> LENGTH: 438
<212> TYPE: PRT
<213> ORGANISM: Artificial Sequence
<220> FEATURE:
<223> OTHER INFORMATION: PID amino acid sequence

<400> SEQUENCE: 6

Met Leu Arg Glu Ser Asp Gly Glu Met Ser Leu Gly Thr Thr Asn Ser
 1               5                  10                  15

Pro Ile Ser Ser Gly Thr Glu Ser Cys Ser Ser Phe Ser Arg Leu Ser
                20                  25                  30

Phe Asp Ala Pro Pro Ser Thr Ile Pro Glu Glu Ser Phe Leu Ser
            35                  40                  45

Leu Lys Pro His Arg Ser Asp Phe Ala Tyr Ala Glu Ile Arg Arg
    50                  55                  60

Arg Lys Lys Gln Gly Leu Thr Phe Arg Asp Phe Arg Leu Met Arg Arg
65                  70                  75                  80

Ile Gly Ala Gly Asp Ile Gly Thr Val Tyr Leu Cys Arg Leu Ala Gly
                85                  90                  95

Asp Glu Glu Glu Ser Arg Ser Ser Tyr Phe Ala Met Lys Val Val Asp
            100                 105                 110

Lys Glu Ala Leu Ala Leu Lys Lys Lys Met His Arg Ala Glu Met Glu
```

-continued

```
            115                 120                 125
Lys Thr Ile Leu Lys Met Leu Asp His Pro Phe Leu Pro Thr Leu Tyr
    130                 135                 140

Ala Glu Phe Glu Ala Ser His Phe Ser Cys Ile Val Met Glu Tyr Cys
145                 150                 155                 160

Ser Gly Gly Asp Leu His Ser Leu Arg His Arg Gln Pro His Arg Arg
                165                 170                 175

Phe Ser Leu Ser Ser Ala Arg Phe Tyr Ala Ala Glu Val Leu Val Ala
                180                 185                 190

Leu Glu Tyr Leu His Met Leu Gly Ile Ile Tyr Arg Asp Leu Lys Pro
            195                 200                 205

Glu Asn Ile Leu Val Arg Ser Asp Gly His Ile Met Leu Ser Asp Phe
    210                 215                 220

Asp Leu Ser Leu Cys Ser Asp Ser Ile Ala Ala Val Glu Ser Ser Ser
225                 230                 235                 240

Ser Ser Pro Glu Asn Gln Gln Leu Arg Ser Pro Arg Arg Phe Thr Arg
                245                 250                 255

Leu Ala Arg Leu Phe Gln Arg Val Leu Arg Ser Lys Lys Val Gln Thr
                260                 265                 270

Leu Glu Pro Thr Arg Leu Phe Val Ala Glu Pro Val Thr Ala Arg Ser
            275                 280                 285

Gly Ser Phe Val Gly Thr His Glu Tyr Val Ala Pro Glu Val Ala Ser
    290                 295                 300

Gly Gly Ser His Gly Asn Ala Val Asp Trp Trp Ala Phe Gly Val Phe
305                 310                 315                 320

Leu Tyr Glu Met Ile Tyr Gly Lys Thr Pro Phe Val Ala Pro Thr Asn
                325                 330                 335

Asp Val Ile Leu Arg Asn Ile Val Lys Arg Gln Leu Ser Phe Pro Thr
                340                 345                 350

Asp Ser Pro Ala Thr Met Phe Glu Leu His Ala Arg Asn Leu Ile Ser
            355                 360                 365

Gly Leu Leu Asn Lys Asp Pro Thr Lys Arg Leu Gly Ser Arg Arg Gly
    370                 375                 380

Ala Ala Glu Val Lys Val His Pro Phe Phe Lys Gly Leu Asn Phe Ala
385                 390                 395                 400

Leu Ile Arg Thr Leu Thr Pro Pro Glu Ile Pro Ser Ser Val Val Lys
                405                 410                 415

Lys Pro Met Lys Ser Ala Thr Phe Ser Gly Arg Ser Ser Asn Lys Pro
                420                 425                 430

Ala Ala Phe Asp Tyr Phe
            435
```